United States Patent [19]

Benavides et al.

[11] Patent Number: 4,788,199
[45] Date of Patent: Nov. 29, 1988

[54] PHARMACOLOGICALLY ACTIVE AMIDES, PROCESSES FOR THEIR PREPARATION AND PHARMACEUTICAL COMPOSITIONS CONTAINING THEM

[75] Inventors: Jesus Benavides, Rueil-Malmaison; Marie-Christine Dubroeucq, Enghien-les-Bains; Gérard Le Fur, Montmorency; Christian Renault, Taverny, all of France

[73] Assignee: Rhone-Poulenc Sante, Courbevoie, France

[21] Appl. No.: 167,126

[22] Filed: Mar. 11, 1988

Related U.S. Application Data

[62] Division of Ser. No. 867,555, May 28, 1986.

[30] Foreign Application Priority Data

May 30, 1985 [FR] France ................ 85 08111

[51] Int. Cl.⁴ .................. A61K 31/505; C07D 239/96
[52] U.S. Cl. ...................... 514/259; 514/227.5; 514/228.2; 514/234.5; 514/237.5; 514/260; 544/58.4; 544/119; 544/128; 544/283; 544/284; 544/286; 544/287; 544/289; 544/292; 544/293; 546/153; 546/157; 546/163; 546/167; 546/173; 546/175
[58] Field of Search ............... 544/284, 58.4, 119, 544/283, 286, 287, 289, 292, 293; 514/222, 228, 230, 232, 233, 234, 235, 259, 260

[56] References Cited

U.S. PATENT DOCUMENTS

| | | | |
|---|---|---|---|
| 3,595,861 | 7/1971 | Bell | 544/283 |
| 4,499,094 | 2/1985 | Dubroeucq et al. | 544/119 |
| 4,684,652 | 8/1987 | Dubroeucq et al. | 544/119 |
| 4,694,000 | 9/1987 | Timmerman et al. | 544/284 |

*Primary Examiner*—Glennon H. Hollrah
*Assistant Examiner*—J. H. Turnipseed
*Attorney, Agent, or Firm*—Stevens, Davis, Miller & Mosher

[57] ABSTRACT

Amides of formula:

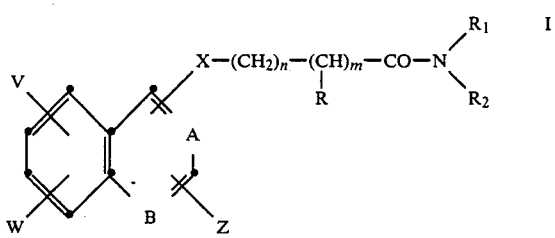

in which
A is

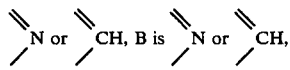

$\diagdown N$ or $\diagdown CH$, B is $\diagdown N$ or $\diagdown CH$, V and W are H, halogen, alkyl (1–3C), alkoxy (1–3C), $NO_2$ or $CF_3$,
Z is bound in the ortho or para position with respect to B and is phenyl, optionally substituted, thienyl or pyridyl, the chain $X-(CH_2)_n-(CHR)_m-CO-NR_1R_2$ is bound in the ortho or para position with respect to B,
R is H or alkyl (1–3C),
$R_1$ and $R_2$ are alkyl (1–6C), cycloalkyl (3–6C), phenyl, phenylalkyl, cycloalkylalkyl, alkenyl (3–6C),
$R_1$ and $R_2$ can also form, with the nitrogen atom to which they are attached, a pyrrolidine, piperidine, morpholine or thiomorpholine ring,
X is $>CH-R_3$, $>N-R_4$, $>SO$, $>SO_2$, $>O$ or $>S$,
$R_3$ is H, alkyl (1–3C),
$R_4$ is alkyl (1–3C)
m=0 or 1 and n=0, 1 or 2, provided that, if X is $>SO$, $>SO_2$ or $>N-R_4$, the sum m+n is equal to at least 1, that, when A and B are N and Z is in the para position with respect to B, X cannot denote the group $>CH-R_3$ and that when A is CH, B is N, Z is in the ortho position with respect to B, X is an oxygen atom, and R is a hydrogen atom, the sum m+n is other than 1, and excluding 2-phenyl-4-quinolyl N,N-dimethylcarbamate, have useful pharmacological activity, e.g. as anxiolytics, anticonvulsants and antiangina agents.

12 Claims, No Drawings

PHARMACOLOGICALLY ACTIVE AMIDES, PROCESSES FOR THEIR PREPARATION AND PHARMACEUTICAL COMPOSITIONS CONTAINING THEM

This is a division of application Ser. No. 867,555, filed May 28, 1986.

The present invention relates to pharmacologically active amides, processes for their preparation, and pharmaceutical compositions containing them.

Amides derived from quinazoline which are useful as tranquillizers are described in U.S. Pat. No. 3,595,861.

The amides of the present invention can be represented by the following formula:

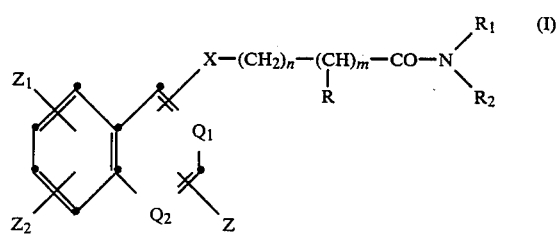

in which $Q_1$ denotes a nitrogen atom or a

group, $Q_2$ denotes a nitrogen atom or a

group, $Z_1$ and $Z_2$, which may be identical or different, denote hydrogen, halogen (e.g. fluorine, chlorine, or bromine) alkyl or alkoxy of 1 to 3 carbon atoms each, nitro, or trifluoromethyl, Z is bound in the ortho or para position with respect to $Q_2$ and denotes phenyl, thienyl, pyridyl, or phenyl substituted by one or two substituents chosen from halogen, alkyl and alkoxy of 1 to 4 carbon atoms each, trifluoromethyl, and nitro, the chain —X—$(CH_2)_n$—$(CHR)_m$—$CONR_1R_2$ is bound in the ortho or para position with respect to $Q_2$, R denotes hydrogen or alkyl of 1 to 3 carbon atoms, $R_1$ and $R_2$, which may be identical or different, denote a linear or branched alkyl of 1 to 6 carbon atoms, cycloalkyl of 3 to 6 carbon atoms, phenyl, phenylalkyl or cycloalkylalkyl in each of which the alkyl contains 1 to 3 carbon atoms and in which the cycloalkyl contains 3 to 6 carbon atoms or alkenyl of 3 to 6 carbon atoms in which the double bond is not situated in the 1,2 position with respect to the nitrogen atom, $R_1$ and $R_2$ can also form, together with the nitrogen atom to which they are attached, a pyrrolidine, piperidine, morpholine or thiomorpholine ring, X denotes >CH—$R_3$, >N—$R_4$, >SO or >$SO_2$, oxygen, or sulphur, $R_3$ denotes hydrogen or alkyl of 1 to 3 carbon atoms, $R_4$ denotes alkyl of 1 to 3 carbon atoms, m is 0 or 1, and n is 0, 1 or 2, provided that, when X denotes >SO, >$SO_2$ or >N—$R_4$, the sum m+n is equal to at least 1, and, when $Q_1$ and $Q_2$ each denote a nitrogen atom and Z is in the para position with respect to $Q_2$, X is not >CH—$R_3$, and, when $Q_1$ denotes

$Q_2$ denotes a nitrogen atom, Z is in the ortho position with respect to $Q_2$, X denotes oxygen and R denotes hydrogen, the sum m+n is other than 1, and excluding 2-phenyl-4-quinolyl N,N-dimethylcarbamate.

The compounds of formula (I) thus correspond to one of the two formulae (Ia) or (Ib)

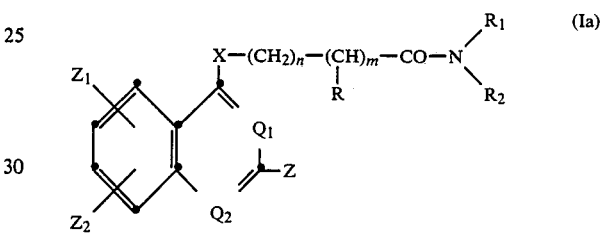

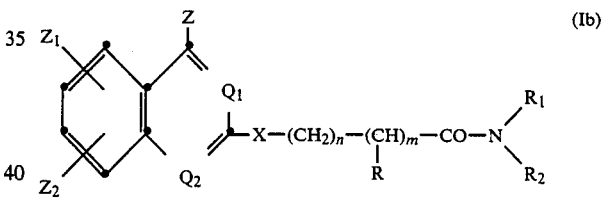

in which $Q_1$, $Q_2$, $Z_1$, $Z_2$, X, Z, $R_1$, $R_2$, n and m have the meanings stated above.

When the chain X—$(CH_2)_n$—$(CHR)_m$—$CO$—$NR_1R_2$ contains 1 or 2 asymmetric carbon atoms, there are several stereoisomers corresponding to the planar formula (I). These various stereoisomers also form part of the invention, as do the addition salts, where they can exist, of the racemic or stereoisomeric compounds of the formula (I) with inorganic or organic acids.

The compounds of the formula (I) in which X denotes oxygen or sulphur, n and m are equal to O and A, B, V, W, Z, $R_1$ and $R_2$ have the same meanings as in the formula (I), i.e. the carbamates and thiocarbamates, can be obtained by the action of a compound of formula:

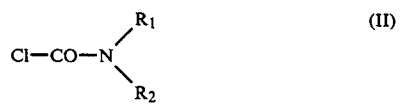

in which $R_1$ and $R_2$ have the same meanings as in the formula (I), on a compound of formula:

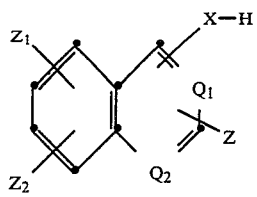 (III)

in which $Q_1$, $Q_2$, $Z_1$, $Z_2$ and Z have the same meanings as in the formula (I) and X denotes oxygen or sulphur.

This reaction is carried out according to processes, known per se, by which an OH or SH group may be converted, respectively, to carbamate or thiocarbamate, such as those described in R. B. WAGNER and H. D. ZOOK, Synthetic Organic Chemistry, J. Wiley, p. 647 (1953) or H. HAGEMANN, Houben Weyl, Methoden der Organischen Chemie, Kohlensäure derivate, B and E4, p. 154 and 297 (1983). This reaction can be performed, for example, in an inert solvent such as tetrahydrofuran or dimethylformamide in the presence of a tertiary organic base such as triethylamine and optionally in the presence of a catalyst such as dimethylaminopyridine, at a temperature of between 20° C. and 70° C.

Most of the compounds of formula (III) are known; the new compounds can be obtained by application or adaptation of the methods described by C. HAUSER and A. REYNOLDS, J.A.C.S., 70, 2402–2404 (1948), GABRIEL, Ber, 29, 131 (1896), H. STEPHEN, J. Chem. Soc., 4420 (1956), D. W. JONES, J. Chem. Soc., 1729 (1969), GABRIEL, Chem. Ber. 18, 3471 (1885), A. KASAHARA, Chem. Ind. 16, 666 (1980) and 4, 121 (1981), W. I. BOYCE, J. Org. Chem., 31, 3807 (1966), SORM, Chem. Listy, 49, 901 (1954).

The compounds of the formula (I) in which X denotes an oxygen or sulphur atom, n equals 0, m equals 1 and $Q_1$, $Q_2$, $Z_1$, $Z_2$, Z, R, $R_1$ and $R_2$ have the same meanings as in the formula (I) can be prepared by the action of a compound of formula:

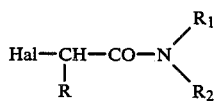 (IV)

in which R, $R_1$ and $R_2$ have the same meanings as in the formula (I) and Hal denotes a halogen (chlorine or bromine) atom, on a derivative of formula (III) in which X denotes an oxygen or sulphur atom, and Q, $Q_2$, $Z_1$, $Z_2$ and Z have the same meanings as in the formula (I). This reaction can be carried out according to known processes, such as that described in Chem. Abst. 95, 203 770K (1981) which consists in working in the presence of a base such as potassium carbonate, preferably in the presence of cuprous iodide, in a solvent such as 2-butanone and at a temperature of between 20° C. and the boiling point of the solvent.

The compounds of formula (I) in which either X denotes an oxygen or sulphur atom, n equals 0, 1 or 2 and m equals 1, or X denotes a group>CH—$R_3$, n equals 0, 1 or 2 and m equals 0 or 1, and $Q_1$, $Q_2$, $Z_1$, $Z_2$, Z, R, $R_1$ and $R_2$ have the same meanings as in the formula (I) can be prepared by the action of an amine of the formula:

 (V)

in which $R_1$ and $R_2$ have the same meanings as in the formula (I), on a derivative of the formula:

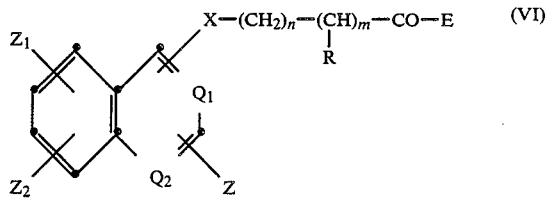 (VI)

in which $Q_1$, $Q_2$, $Z_1$, $Z_2$, Z, R and n have the same meanings as in the formula (I), E denotes an alkoxy group containing 1 to 4 carbon atoms, an alkoxycarbonyloxy group containing 2 to 5 carbon atoms, a chlorine atom or an N-imidazolyl residue, either X denotes an oxygen or sulphur atom, m is equal to 1, or X denotes a group>CH—$R_3$, m is equal to 0 or 1 and $R_3$ denotes a hydrogen atom or an alkyl group containing 1 to 3 carbon atoms.

This reaction can be carried out according to processes, known per se, by means of which a carboxylic acid ester, carboxylic acid chloride, mixed anhydride or azolide may be converted to carboxamide, such as those described by C. A. BUEHLER and D. E. PEARSON, Survey of Organic Synthesis, Wiley Interscience, p. 894, 1970.

When E is an alkoxy group containing 1 to 4 carbon atoms, an advantageous process consists in heating the ester of formula (VI) to a temperature of between 120° C. and 180° C. In the amine of formula (V), present in excess.

When E is a chlorine atom, the acid chloride of formula (VI) can be treated with an excess of the amine of formula (V) in an inert solvent such as toluene, chloroform or methylene chloride, at a temperature of between 20° C. and the boiling point of the solvent used. The excess of amine used, which performs the role of a base which neutralizes the hydrochloric acid formed in the reaction, is at least one equivalent, i.e. the total amount of amine employed is at least two equivalents. in the case where $Q_1$ or $Q_2$ denotes a nitrogen atom, the acid chloride of formula (VI) can be used in the form of hydrochloride, provided that at least one further equivalent of the amine of formula (V) is employed so as to change the acid chloride from the hydrochloride form to the free base form.

When E is a chlorine atom, the acid chloride of formula (VI) can also be reacted with the amine of formula (V) in the presence of a tertiary amine such as triethylamine, in an inert solvent such as toluene, chloroform or methylene chloride, at a temperature of between 20° C. and the boiling point of the solvent.

The acid chloride of formula (VI) can also be reacted with the amine of formula (V) in pyridine, which serves both as a base which binds the acid formed and as a solvent.

When E is an alkoxycarbonyloxy group containing 2 to 5 carbon atoms, the mixed anhydride of formula (VI) can be treated with the amine of formula (V) in an inert solvent such as benzene, toluene, chloroform or methylene chloride, at a temperature of between −5° C. and +25° C.

When E is an N-imidazolyl residue, the azolide of formula (VI) can be reacted with the amine of formula (V) in an inert solvent such as tetrahydrofuran or dimethylformamide, at a temperature of between 20° C. and the boiling point of the solvent.

The compounds of formula (VI) can be obtained by the action on an acid of formula:

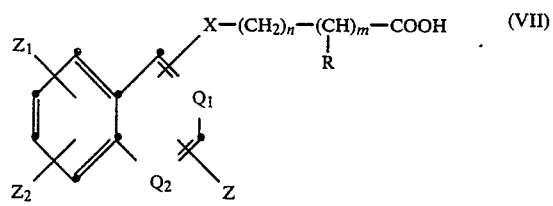

in which $Q_1$, $Q_2$, $Z_1$, $Z_2$, Z, X, R, m and n have the same meanings as in the formula (VI), of a low molecular weight (1-4C) saturated aliphatic alcohol such as methanol or ethanol (cases where E is an alkoxy group), a chlorinating agent such as thionyl chloride (cases where E is a chlorine atom), a low molecular weight (1-4C) alkyl chloroformate such as methyl or ethyl chloroformate (cases where E is an alkoxycarbonyloxy group) or carbonyldiimidazole (cases where E is an N-imidazolyl residue).

The reaction of the acid of formula (VII) with the low molecular weight saturated aliphatic alcohol can be carried out by heating the acid of formula (VII) to refluxing temperature in the said alcohol, in the presence of an inorganic acid such as sulphuric acid or hydrochloric acid.

The reaction of the acid of formula (VII) with the chlorinating agent can be carried out in the absence of solvent or in an inert solvent such as chloroform or toluene, preferably at the refluxing temperature of the medium.

The reaction of the acid of formula (VII) with the low molecular weight (1-4C) alkyl chloroformate can be carried out in an inert solvent such as chloroform or methylene chloride, at a temperature of −5° C. to +25° C., in the presence of a tertiary amine such as triethylamine, and the mixed anhydride thereby formed can then be reacted in situ with the amine of the formula (V).

The reaction of the acid of formula (VII) with carbonyldiimidazole can be performed, under nitrogen, in an inert solvent such as tetrahydrofuran or dimethylformamide, at a temperature of between −5° C. and +30° C. The azolide thereby formed can then be reacted in situ with the amine of formula (V).

Some acids of formula (VII) are known, such as 2-phenyl-4-quinolinepropionic acid [J. HANNS, Ber, 58, 2799 (1925)]. Those which are not known can be prepared by application or adaptation of the methods described in Examples 7, 8, 10 to 14, 20, 21, 22, 24, 25, 26, 43, 44, 51, 54 to 56, 68, 85 and 86, and in R. B. WAGNER and H. D. ZOOK, Synthetic Organic Chemistry, J. Wiley, p. 411–478 (1953), and C. A. BUEHLER and D. E. PEARSON, Survey of Organic Synthesis, Wiley Interscience, p. 655-710 (1970).

The compounds of formula (I) in which $Q_1$ is a  group, $Q_2$ is a nitrogen atom, Z is bound in the ortho position with respect to $Q_2$, the chain —X—$(CH_2)_n$—$(CHR)_m$—CO—$NR_1R_2$ is bound in the para position with respect to $Q_2$, X denotes a group >CH—$R_3$, $R_3$ denotes an alkyl group containing 1 to 3 carbon atoms, m equals 0 and n equals 0, $Z_1$, $Z_2$, Z, $R_1$ and $R_2$ having the same meanings as in the formula (I), can be prepared by alkylation of the compounds of formula:

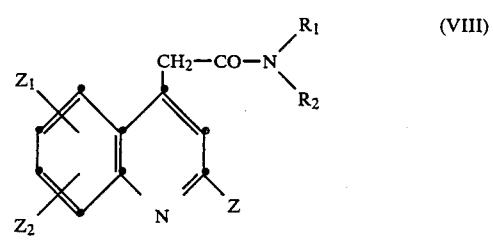

in which $Z_1$, $Z_2$, Z, $R_1$ and $R_2$ have the same meanings as in the formula (I), with a compound of formula $R_3$—Hal in which $R_3$ is an alkyl group containing 1 to 3 carbon atoms and Hal denotes a halogen (bromine or iodine) atom. This reaction can be performed according to known methods, such as those described by J. C. STOWELL, Carbanions in Organic Synthesis, p. 161 (1979), Wiley Sons.

An advantageous process consists in working under nitrogen at a temperature of between −70° C. and 0° C., in the presence of a strong base such as lithium diisopropylamide.

The compounds of formula (I) in which X denotes a sulphinyl or sulphonyl group, the sum m+n is equal to at least 1 and $Q_1$, $Q_2$, $Z_1$, $Z_2$, Z, R, $R_1$ and $R_2$ have the same meanings as in the formula (I), can be prpared by oxidation of the corresponding compounds of formula (I) in which X denotes a sulphur atom.

This reaction can be performed according to processes, known per se, by means of which a sulphide may be converted to sulphoxide or sulphone, such as those described by D. BARTON and W. D. OLLIS, Comp. Organic Chemistry, volume 3, p. 124 and 174 (1979), Pergamon Press.

These processes consist in oxidizing a sulphide to sulphoxide or a sulphoxide to sulphone by means of an oxidizing agent such as hydrogen peroxide, sodium metaperiodate or a peracid, in a solvent such as an alcohol, e.g. ethanol, or an acid, e.g. acetic acid, at a temperature of between 0° C. and 80° C.

The compounds of formula (I) in which X denotes a group >N—$R_4$, m equals 1, $Q_1$, $Q_2$, $Z_1$, $Z_2$, Z, R, $R_1$, $R_2$ and n have the same meanings as in the formula (I) and $R_4$ denotes an alkyl group containing 1 to 3 carbon atoms, can be prepared by reaction of an aminoalkylamide of formula:

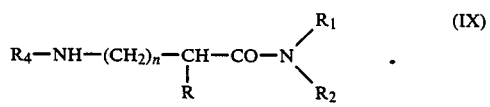

with a derivative of formula:

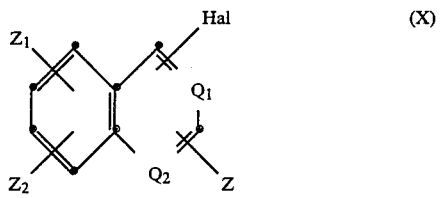

In the formulae (IX) and (X), $Q_1$, $Q_2$, $Z_1$, $Z_2$, Z, R, $R_1$, $R_2$ and n have the same meanings as in the formula (I), $R_4$ denotes an alkyl group containing 1 to 3 carbon atoms and Hal denotes a halogen (chlorine or bromine) atom.

This reaction can be carried out according to processes, known per se, by means of which aromatic nucleophilic substitutions may be performed on halogenated deriVatives such as those described by A. R. SURVEY et al., J. Am. Chem. Soc., 73, 2623 (1951).

In cases where $Q_1$ or $Q_2$ is a nitrogen atom, an advantageous process consists in working in the presence of phenol at a temperature of between 125° C. and 180° C.

The compounds of formula (I) in which $Q_1$ and $Q_z$ each denote a nitrogen atom, Z is bound in the ortho position with respect to $Q_2$, the chain—X—$(CH_2)_n$—$(CHR)_m$—CO—$NR_1R_2$ is bound in the para position with respect to $Q_2$, X is a group >CH—$R_3$, $R_3$ is a hydrogen atom, n equals 1, m equals 0 and $Z_1$, $Z_2$, Z, $R_1$ and $R_2$ have the same meanings as in the formula (I), can be prepared from compounds of formula:

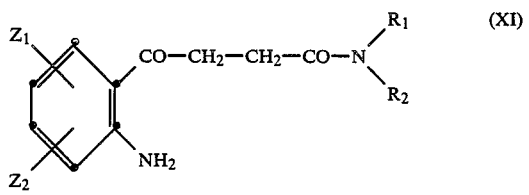

in which $Z_1$, $Z_2$, $R_1$ and $R_2$ have the same meanings as in the formula (I), by the action of a chloride ZCOCl in which Z has the same meanings as in the formula (I), and cyclization.

This reaction can be performed according to W. L. F. ARMAREGO, Fused Pyrimidines, Part I, quinazolines, p. 39, Intersciences Publishers, Wiley, 1967.

This process consists in treating the compound (XI) with the acid chloride ZCOCl, in an inert solvent such as chloroform, at between 20° C. and 25° C., and then with ammonium acetate, preferably in the presence of acetic acid, at a temperature of between 100° C. and 120° C.

The enantiomers of the compounds of formula (I) in which the chain—X—$(CH_2)_n$—$(CHR)_m$—CO—$NR_1R_2$ contains one or two asymmetric carbon atoms can be obtained by resolving the racemates, for example by chromatography on a chiral column according to W. H. PIRKLE et al, Asymmetric Synthesis, vol. 1, Academic Press (1983) or alternatively by synthesis from chiral precursors.

The reaction mixtures obtained by the various processes described above are treated according to conventional physical methods (evaporation, extraction, distillation, crystallization, chromatography) or chemical methods, where appropriate (salt formation and regeneration of the base or acid), in order to isolate the compounds of the formula (I) in the pure state.

Where possible, the compounds of formula (I), in the form of free base, can optionally be converted to addition salts with an inorganic or organic acid by the action of such an acid in an organic solvent such as an alcohol, a ketone, an ether or a chlorinated solvent.

The compounds of formula (I) and their salts possess advantageous pharmacological properties. These compounds bind to peripheral type benzodiazepine receptors, and are consequently useful as anxiolytics, anticonvulsants and antianginals, and for the treatment of immuno-deficiency states.

The affinity of the compounds of formula (I) for peripheral type benzodiazepine receptor sites has been determined by the procedure of BRAESTRUP et al., Proc. Natl. Acad. Sci. USA, 74, 3805 (1977) on rat kidney membranes, by measurinq the ability of the new compound to displace $^3H$-PK11195 [N-methyl-N-(1-methylpropyl)-1-(2-chlorophenyl)-3-isoquinolinecarboxamide] from its binding site. This affinity (Ki) is between 0.001 and 1.5 μM, as measured by the formula $$Ki = \frac{IC_{50}}{1 + \frac{C}{KD}}$$

where C is the concentration of $^3H$-PK11195, $K_D$ is an affinity constant characteristic of PK-11195 and $IC_{50}$ is the concentration of compound under test required to inhibit by 50% the binding of $^3H$-PK11195.

The compounds according to the invention possess low toxicity. Their oral $LD_{50}$ in mice is greater than 200 mg/kg. The $LD_{50}$ values were calculated after 3 days of observation by the cumulative method of J. J. REED and H. MUENCH, Amer. J. Hyg., 27, 493 (1938).

Of special value are the compounds of formula (I) in which $Z_1$ and $Z_2$, which may be identical or different, each denote hydrogen or alkyl of 1 to 3 carbon atoms, Z is bound in the ortho position with respect to $Q_2$ and denotes phenyl or phenyl substituted by alkyl or alkoxy of 1 to 4 carbon atoms each, nitro, trifluoromethyl or thienyl, the chain —X—$(CH_2)_n$—$(CHR)_m$—CO—$NR_1R_2$ is bound in the para position with respect to $Q_2$, R denotes hydrogen or alkyl of 1 to 3 carbon atoms, $R_1$ and $R_2$, which may be identical or different, each denote linear or branched alkyl of 1 to 6 carbon atoms each or phenyl, $R_1$ and $R_2$ can also form, together with the nitrogen atom to which they are attached, a piperidine or morpholine ring, X denotes >—CH—$R_3$ oxygen or sulphur, $R_3$ denotes hydrogen, m equals 0 or 1, n equals 0, 1 or 2, and either $Q_1$ denotes >CH and $Q_2$ denotes nitrogen or $Q_1$ denotes nitrogen and $Q_2$ denotes >CH, or $Q_1$ and $Q_2$ both denote nitrogen, provided that, when $Q_1$ denotes >CH, $Q_2$ denotes nitrogen, Z is in the ortho position with respect to $Q_2$, X denotes oxygen and R denotes hydrogen, the sum m+n is other than 1, and excluding 2-phenyl-4-quinolyl N,N-dimethylcarbamate.

The following compounds are of special value:
N,N-Diethyl-2-phenyl-4-quinazolinepropanamide
N,N-Diethyl-2-(3-methoxyphenyl)-4-quinazolinepropanamide
N,N-Diethyl-3-phenyl-1-isoquinolinepropanamide N,N-Diethyl-2-phenyl-4-quinolineacetamide
N,N-Diethyl-α-methyl-2-phenyl-4-quinazolinepropanamide propanamide
N-Methyl-N-phenyl-2-phenyl-4-quinazolinepropanamide
1-[3-(2-Phenyl-4-quinazolinyl)propionyl]piperidine
N,N-Diethyl-2-(4-nitrophenyl)-4-quinazolinepropanamide panamide
N,N-Diethyl-α-methyl-3-phenyl-1-isoquinolinepropanamide propanamide
N,N-Diethyl-α-methyl-2-phenyl-4-quinolinepropanamide amide
Laevorotatory N,N-diethyl-α-methyl-2-phenyl-4-quinolinepropanamide,
N,N-Diethyl-2-(3-trifluoromethylphenyl)-4-quinazolinepropanamide
N,N-Diethyl-2-thienyl-4-quinazolinepropanamide
N,N-Diethyl-8-methyl-2-phenyl-4-quinazolinepropanamide amide
4-Phenyl-2-quinolyl diethylcarbamate
2-Phenyl-4-quinazolyl diethylcarbamate
3-Phenyl-1-isoquinolyl diethylcarbamate
3-(4-Methylphenyl)-1-isoquinolyl diethylcarbamate
N,N-Diethyl-2-[(2-phenyl-4-quinolyl)oxy]propanamide
N,N-Diethyl-(2-phenyl-4-quinazolinyl)oxyacetamide
N,N-Diethyl-(3-phenyl-1-isoquinolyl)oxyacetamide
N,N-Diethyl-2-[(3-phenyl-1-isoquinolyl)oxy]propanamide amide
N,N-Diethyl-2-[(2-phenyl-4-quinazolinyl)oxy]propanamide
Dextrorotatory N,N-Diethyl-2-[(2-phenyl-4-quinazolinyl)oxy]propanamide
N,N-Diethyl-2-[(2-phenyl-4-quinolyl)thio]propanamide
4-[3-(2-phenyl-4-quinolyl)propionyl]morpholine
2-(4-Methoxyphenyl)-4-quinolyl diethylcarbamate
6-Nitro-2-phenyl-4-quinolyl diethylcarbamate
2-(4-Methylphenyl)-4-quinolyl diethylcarbamate
2-(2-Fluorophenyl)-4-quinolyl diethylcarbamate
2-(2-Thienyl)-4-quinolyl diethylcarbamate
2-(3-Chlorophenyl)-4-quinolyl diethylcarbamate.

For medicinal use, the compounds of formula (I) can be used as they are or in the state of salts with a pharmaceutically acceptable strong acid where such salts exist.

As pharmaceutically acceptable salts, there may be mentioned the addition salts with inorganic acids, such as hydrochlorides, sulphates, nitrates or phosphates, or organic acids, such as acetates, propionates, succinates, benzoates, fumarates, theophyllineacetates, salicylates, phenolphthalinates, methylenebis (β-hydroxynaphthoates) or substitution derivatives of these compounds.

The examples which follow show how the invention can be put into practice.

EXAMPLE 1

A mixture of ethyl 2-phenyl-4-quinazolinepropionate (4.3 g) and diethylamine (30 cc) is heated to 250°C. for 40 hours. After the mixture is cooled, the excess diethylamine is evaporated off. The residue is chromatographed on silica gel with a cyclohexane/ethyl acetate (1:1 by volume) mixture as eluant. The product (3.2 g) is recovered and recrystallized in isopropyl ether. N,N-Diethyl-2-phenyl-4-quinazolinepropanamide (2.2 g), m.p. 103° C., is obtained.

Ethyl 2-phenyl-4-quinazolinepropionate is prepared by esterification of the corresponding acid by means of ethanol in the presence of sulphuric acid.

EXAMPLE 2

The procedure is as in Example 1, starting with ethyl 2-(3-methoxyphenyl)-4-quinazolinepropionate (1.2 g) and diethylamine (30 cc). After chromatography on silica gel with a cyclohexane/ethyl acetate (1:1 by volume) mixture as eluant, and crystallization in isopropyl ether, N,N-diethyl-2-(3-methoxyphenyl)-4-quinazolinepropanamide (0.36 g), m.p. 87° C., is obtained.

Ethyl 2-(3-methoxyphenyl)-4-quinazolinepropionate is prepared according to the following process:

3-(2-Aminobenzoyl)propionic acid (26.7 g) and concentrated sulphuric acid (25 cc) in absolute ethanol (250 cc) are stirred for 17 hours at room temperature (approximately 20° C.). The ethanol is evaporated off under reduced pressure, water (200 cc) and ethyl acetate (200 cc) are added and potassium carbonate is added until the pH is 8. The mixture is filtered, and the aqueous phase decanted and re-extracted with ethyl acetate (2×100 cc). The organic phase is dried over magnesium sulphate, filtered and evaporated to dryness under reduced pressure. Ethyl 3-(2-aminobenzoyl)propionate (24.8 g) is obtained in the form of an oil. The proton NMR spectrum in deuterated chloroform shows the following characteristics:

| CH$_2$—C$\underline{H}_3$ | δ: 1.2 ppm | C$\underline{H}_2$—COOC$_2$H$_5$ | δ: 2.8 ppm |
|---|---|---|---|
| C$\underline{H}_2$—CH$_3$ | δ: 4.2 ppm | H$_6$ | δ: 7.9 ppm |
| Ar—CO—C$\underline{H}_2$— | δ: 3.3 ppm | H$_4$ | δ: 7.3 ppm |
| NH$_2$ | δ: 5.7 ppm | H$_3$ and H$_5$ | δ: 6.7 ppm |

3-Methoxybenzoyl chloride (2.81 cc) is added at 5° C. to ethyl 3-(2-aminobenzoyl)propionate (2.21 g) and triethylamine (4.2 cc) in chloroform (25 cc). The mixture is left for 1 hour at room temperature (approximately 20° C.), water (25 cc) is added and the mixture decanted. The organic phase is evaporated under reduced pressure and the residue taken up with ammonium acetate (17 g). The mixture is brought to 100° C. for 7 hours and the acetic acid formed is then evaporated off under reduced pressure. The residue is poured into water (100 cc) and the aqueous phase extracted with ethyl acetate (3×50 cc). The aqueous phase is dried over magnesium sulphate, filtered and evaporated to dryness under reduced pressure. The residual product is chromatographed in silica gel with a cyclohexane/ethyl acetate (1:1 by volume) mixture as eluant. After recrystallization in ethanol, ethyl 2-(3-methoxyphenyl)-4-quinazolinepropionate (1.5 g), m.p. 70° C., is obtained.

3-(2-Aminobenzoyl)propionic acid can be prepared according to D. E. RIVETT et al., Aust. J. Chem., 24, 2717 (1971).

EXAMPLE 3

The procedure is as in Example 1, starting with ethyl 1-phenyl-3-isoquinolinepropionate (4.2 g) and diethylamine (20 cc). After an initial chromatographic separation on silica gel with a cyclohexane/ethyl acetate (1:1 by volume) mixture as eluant, followed by a second chromatographic separation with ethyl acetate as eluant and crystallization in petroleum ether, N,N-diethyl-1- phenyl-3-isoquinolinepropanamide (0.6 g), m.p. 70° C., is obtained.

Ethyl 1-phenyl-3-isoquinolinepropionate is prepared according to the following technique:

A mixture of 3-methyl-1-phenylisoquinoline (20 g), N-bromosuccinimide (17.8 g) and benzoyl peroxide (0.2 g) in carbon tetrachloride (685 cc) is brought to boiling for 20 hours. The mixture is filtered and the filtrate evaporated under reduced pressure. The residue is chromatographed on silica gel with a cyclohexane/ethyl acetate (9:1 by volume) mixture as eluant. 3-Bromomethyl-1-phenylisoquinoline (8.7 g), m.p. 109° C., is recovered.

A solution of diethyl malonate (17.9 g) in anhydrous tetrahydrofuran (100 cc) is added dropwise under nitrogen to sodium hydride (3.36 g, 80% strength in oil) and anhydrous tetrahydrofuran (80 cc). After 1 hour's stirring, a solution of 3-bromomethyl-1-phenylisoquinoline (8.3 g) in tetrahydrofuran (100 cc) is added dropwise, and the mixture is left with stirring at room temperature (approximately 20° C.) for 1 hour. Water (200 cc) is added and the aqueous phase extracted with ethyl acetate (3×200 cc). The organic phase is dried over magnesium sulphate, filtered and evaporated to dryness under reduced pressure. The residue is chromatographed on silica gel with a cyclohexane/ethyl acetate (4:1 by volume) mixture as eluant. An oil (9.6 g) is recovered, taken up in concentrated hydrochloric acid (95 cc) and brought to boiling for 20 hours. After the mixture is cooled, water (200 cc) is added, the aqueous phase is washed with ethyl acetate (2×50 cc), potassium hydroxide solution is added until the pH is 5 and the mixture is extracted with chloroform (3×50 cc). The organic phase is dried over magnesium sulphate and evaporated to dryness under reduced pressure. 1-Phenyl-3-isoquinolinepropanoic acid (2.9 g), m.p. 146° C., is obtained.

1-Phenyl-3-isoquinolinepropanoic acid (2 g) and concentrated sulphuric acid (2 cc) in absolute ethanol (20 cc) are stirred for 20 hours at room temperature (approximately 20° C.). The mixture is diluted with water (100 cc), alkalinised to pH 9 with concentrated ammonia solution and extracted with methylene chloride (3×50 cc). The organic phase is dried over magnesium sulphate, filtered and evaporated to dryness under reduced pressure. Ethyl 1-phenyl-3-isoquinolinepropionate (1.9 g) is obtained in the form of an oil, the proton NMR spectrum of which, in deuterated chloroform, has the following characteristics:

| $H_8$ | δ: 8 ppm | | |
|---|---|---|---|
| | other aromatic H δ: 7.3 to 8 ppm | | |
| Ar—$CH_2$ | δ: 3.2 ppm | $CH_2$—$CH_3$ | δ: 4.2 ppm |
| —$CH_2$—$\underline{CH}_2$— | δ: 2.9 ppm | $CH_3$ | δ: 1.2 ppm |

3-Methyl-1-phenylisoquinoline can be prepared according to W. M. WHALEY et al., J. Org. Chem., 14, 650 (1949).

EXAMPLE 4

The procedure is as in Example 1, starting with ethyl 3-phenyl-1-isoquinolinepropionate (6.1 g) and diethylamine (30 cc). The crude product is purified by means of 4 successive chromatographic separations on silica gel, using a cyclohexane/ethyl acetate (7:3 by volume) mixture as eluant. N,N-Diethyl-3-phenyl-1-isoquinolinepropanamide (1.4 g), m.p. 58° C., is obtained.

Ethyl 3-phenyl-1-isoquinolinepropionate is prepared according to the following process:

A mixture of 1-methyl-3-phenylisoquinoline (21 g), N-bromosuccinimide (30.6 g) and benzoyl peroxide (1 g) in carbon tetrachloride (730 cc) is brought to boiling for 48 hours. After being cooled, the mixture is filtered and the filtrate evaporated to dryness under reduced pressure. The residue is chromatographed on silica gel with a toluene/methanol (98:2 by volume) mixture as eluant. After crystallization in isopropyl ether, 1-bromomethyl-3-phenylisoquinoline (11 g), m.p. 84° C., is obtained.

Sodium hydride (6.5 g, 80% strength in oil) is placed with tetrahydrofuran (160 cc) under nitrogen, and a solution of diethyl malonate (34.9 g) in anhydrous tetrahydrofuran (200 cc) is added dropwise. After 1 hour's stirring at room temperature (approximately 20° C.), a solution of 1-bromomethyl-3-phenylisoquinoline (16.2 g) in anhydrous tetrahydrofuran (200 cc) is added. After 20 hours' stirring at 20° C., water (200 cc) is added and the aqueous phase extracted with ethyl acetate. The organic phase is dried and evaporated to dryness under reduced pressure. The residual product is chromatographed on silica gel with a cyclohexane/ethyl acetate (8:2 by volume) mixture as eluant. The product (11.5 g) is recovered, taken up in concentrated hydrochloric acid (115 cc) and brought to boiling for 20 hours. Water (200 cc) is added, and the precipitate is filtered off and washed with water and acetone. 3-Phenyl-1-isoquinolinepropanoic acid (6.7 g) m.p. 160° C., is obtained.

3-Phenyl-1-isoquinolinepropanoic acid (6.7 g) and concentrated sulphuric acid (7 cc) in ethanol (0 cc) are stirred for 20 hours at 20° C. The solution is poured into water (400 cc) and the aqueous phase alkalinised with concentrated ammonia solution. The mixture is extracted with methylene chloride (3×100 cc), and the organic phase dried and evaporated to dryness under reduced pressure. Ethyl 3-phenyl-1-isoquinolinepropionate (6.3 g), m.p. 60° C., is obtained.

1-Methyl-3-phenylisoquinoline can be prepared according to S. GOSZCZYNSKI, Rocznicki Chem., 38(5), 893–5 (1964); Chem. Abst. 62, 16188 a (1965).

EXAMPLE 5

The procedure is as in Example 1, starting with ethyl 2-phenyl-4-quinolineacetate (3 g) and diethylamine (60 cc).

The residue is chromatographed on silica gel with a cyclohexane/ethyl acetate (50:50 by volume) mixture as eluant. After recrystallization in ethyl acetate, N,N-diethyl-2-phenyl-4-quinolineacetamide (2.05 g), m.p. 86° C., is isolated.

Ethyl 2-phenyl-4-quinolineacetate is prepared according to the following process:

Diisopropylamine (12.9 cc) is added to dry tetrahydrofuran (40 cc) under an atmosphere of nitrogen. The solution is stirred and then cooled to −70° C. A 1.6M solution (46 cc) of butyllithium in hexane is then introduced in the course of 15 minutes, then, after stabilization of the temperature at −60° C., 2-phenyllepidine (8.1 g) in tetrahydrofuran (20 cc) is introduced in the course of 15 minutes, and the mixture is then returned to room temperature (approximately 20° C.). This solution is added dropwise and under nitrogen to a solution, which has been cooled beforehand to −(20° C. of diethyl carbonate (9 cc) in tetrahydrofuran 50 cc). After the introduction is complete, the mixture is left with stirring at room temperature (approximately 20° C.) for one hour.

There are then added, dropwise, absolute ethanol (25 cc), followed by glacial acetic acid (10 cc) and finally water (100 cc). The tetrahydrofuran is evaporated off under reduced pressure and the aqueous phase taken up with ethyl ether (200 cc). The ether phase is washed with water, dried over magnesium sulphate and evaporated under reduced pressure. The residue is taken up with toluene (100 cc), which is evaporated off again in order to remove the acetic acid.

The residue is chromatographed on silica gel with a cyclohexane/ethyl acetate (90:10 by volume) mixture as eluant. Ethyl 2-phenyl-4-quinolineacetate (7 g) is obtained in the form of a yellow oil. This product can be taken up in acetone and, after addition of a solution of hydrochloric acid in ethyl ether, ethyl 2-phenyl-4-quinolineacetate hydrochloride (5.13 g), m.p. 180° C., is isolated.

2-Phenyllepidine can be prepared according to GOLDBERG et al., J. Amer. Chem. Soc., 77, 3647 (1955).

EXAMPLE 6

Diisopropylamine (1.84 cc) is added to dry tetrahydrofuran (25 cc) under an atmosphere of nitrogen. The solution is stirred and cooled to −b 70° C., and a 1.6M solution (7 cc) of butyllithium in hexane is introduced into it in the course of 10 minutes.

After stabilization of the temperature at −70° C., a solution of N,N-diethyl-2-phenyl-4-quinolineacetamide (2.4 g), prepared according to Example 5, in tetrahydrofuran (10 cc) is introduced. The mixture is left for 30 minutes with stirring at −70° C., and a solution of methyl iodide (0.58 cc) in tetrahydrofuran (10 cc) and hexamethylphosphoramide (0.52 cc) are then added slowly.

The mixture is stirred for 3 hours at −70° C. and then for 30 minutes at −50° C. Absolute ethanol (3 cc) is then added dropwise, followed by glacial acetic acid (2 cc). The temperature is brought up to 0° C., water (50 cc) is then added and the mixture is extracted with ethyl ether (3×50 cc). The organic phase is washed with water, dried over magnesium sulphate and evaporated under reduced pressure. After recrystallization of the residue in isopropyl ether, N,N-diethyl-α-methyl-2-phenyl-4-quinolineacetamide (1.65 g), m.p. 132° C., is obtained.

EXAMPLE 7

Carbonyldiimidazole (3 g) is added under nitrogen to a suspension of α-methyl-2-phenyl-4-quinazolinepropanoic acid (2.67 g) in anhydrous tetrahydrofuran (30 cc). After 2 hours' stirring, diethylamine (6 cc) is added and the mixture is stirred for a further 4 hours. Water (150 cc) and ethyl acetate (100 cc) are added. The mixture is decanted, the aqueous phase extracted with ethyl acetate (2×100 cc), and the organic phase dried over magnesium sulphate and evaporated to dryness. The residue is chromatographed on silica gel, initially with a cyclohexane/ethyl acetate (1:1 by volume) mixture and then a second time with a cyclohexane/ethyl acetate (8:2 by volume) mixture.

After recrystallization in ispropyl ether, N,N-diethyl-α-methyl-2-phenyl-4-quinazolinepropanamide (1 g), m.p. 124° C. is obtained.

α-Methyl-2-phenyl-4-quinazolinepropanoic acid is prepared according to the following process:

A mixture of 4-methyl-2-phenylquinazoline (15 g), N-bromosuccinimide (13.3 g) and benzoyl peroxide (1.65 g) in carbon tetrachloride (150 cc) is brought for 3 hours to 90° C. The mixture is filtered, the filtrate evaporated and the residue chromatographed on silica gel with a cyclohexane/ethyl acetate (9:1 by volume) mixture as eluant. 4-Bromomethyl-2-phenylquinazoline (11 g), m.p. 110° C., is obtained.

A solution of diethyl methylmalonate (23 g) in anhydrous tetrahydrofuran (100 cc) is added under nitrogen to sodium hydride (4 g, 80% strength in oil) and anhydrous tetrahydrofuran (60 cc). After 1 hour's stirring, a solution of 4-bromomethyl-2-phenylquinazoline (9.9 g) in anhydrous tetrahydrofuran (100 cc) is added, and the mixture is stirred for a further 2 hours at room temperature (approximately 20° C.). Water (100 cc) is added and the mixture is extracted with ethyl acetate (3×100 cc). The organic phase is dried over magnesium sulphate and then evaporated to dryness under reduced pressure. The residue is taken up in concentrated hydrochloric acid (100 cc) and acetic acid (100 cc) and the mixture is brought to 110° C. for 24 hours. After the mixture has cooled, the precipitate is filtered off and washed with water and then ispropyl ether. After being dried, α-methyl-2-phenyl-4-quinazolinepropanoic acid (4 g), m.p. 180° C., is obtained.

4-Methyl-2-phenylquinazoline can be obtained according to W. L. F. AMAREGO, Fused Pyrimidines, Quinazolines Part I p. 39, Intersciences Publishers (1967).

EXAMPLE 8

The procedure is as in Example 7, starting with 2-phenyl-4-quinazolinepropanoic acid (1.95 g), carbonyldiimidazole (1.36 g) and N-methylaniline (3 cc) in anhydrous tetrahydrofuran (40 cc). After purification by chromatography on silica gel with ethyl acetate as eluant, and recrystallization in an ethyl acetate/isopropyl ether (1:5 by volume) mixture, N-methyl-N-phenyl-2-phenyl-4-quinazolinepropanamide (0.63 g), m.p. 116° C., is obtained.

2-Phenyl-4-quinazolinepropanoic acid is prepared according to the following process:

Sodium hydride (5.4 g, 80% strength in oil) is placed under nitrogen with anhydrous tetrahydrofuran (250 cc) and then, with the mixture cooled to about 5° C., diethyl malonate (25.6 g) is added. When the evolution of hydrogen has ceased, a solution of 4-bromomethyl-2-phenylquinazoline (23.9 g) in anhydrous tetrahydrofuran (100 cc) is added. After 1 hour's stirring at room temperature (approximately 20° C.), acetic acid (25 cc) is added, the solvent evaporated under reduced pressure and the residue taken up in concentrated hydrochloric acid (150 cc) and acetic acid (150 cc). The mixture is brought to 120° C. for 15 hours and evaporated again, water (200 cc) and ethyl ether (150 cc) are added and the mixture is alkalinised to pH 11 with sodium hydroxide solution. The organic phase is decanted and the aqueous solution washed with ethyl ether (2×100 cc). The aqueous phase is adjusted to pH 4 and extracted with ethyl acetate (2×100 cc). The organic phase is dried over magnesium sulphate and evaporated to dryness under reduced pressure. The residue is crystallized in ethyl acetate. 2-Phenyl-4-quinazolinepropanoic acid (9 g), m.p. 159° C., is obtained.

EXAMPLE 9

The procedure is as in Example 7, starting with 2-phenyl-4-quinazolinepropanoic acid (1.95 g), carbonyldiimidazole (1.36 g) and piperidine (1.38 cc) in tetrahydrofuran (40 cc). After chromatography on silica gel with ethyl acetate as eluant, and recrystallization in an ethyl acetate/isopropyl ether (1:2 by volume) mixture, 1-[3-(2-phenyl-4-quinazolinyl)propionyl]piperidine (0.88 g), m.p. 115° C., is obtained.

EXAMPLE 10

The procedure is as in Example 7, starting with 2-(2-chlorophenyl)-4-quinazolinepropanoic acid (2.17 g), carbonyldiimidazole (1.35 g) and diethylamine (1.5 cc) in tetrahydrofuran (20 cc).

After chromatography on silica gel with ethyl acetate as eluant, and crystallization in isopropyl ether, N,N-diethyl-2-(2-chlorophenyl)-4-quinazolinepropanamide (1.5 g), m.p. 90° C., is obtained.

2-(2-Chlorophenyl)-4-quinazolinepropanoic acid is prepared according to the following process:

Ortho-chlorobenzoyl chloride (3.2 cc) is added at 5° C. to a solution of ethyl 3-(2-aminobenzoyl)propionate (3.3 g) and triethylamine (6.3 cc) in chloroform (35 cc). The mixture is stirred for 20 hours at room temperature (approximately 20° C.) and the solvent removed by evaporation under reduced pressure. The residue is taken up with ethyl ether (50 cc), the insoluble material filtered off and the filtrate evaporated.

The residual product is mixed with ammonium acetate (15 g) and brought to 110° C. for 4 hours. After the mixture is cooled, water (100 cc) is added and the aqueous phase extracted with chloroform (3×50 cc). The solvent is removed under reduced pressure and the residue taken up in ethanol (50 cc) and concentrated sodium hydroxide solution (10 cc). The mixture is brought for 1 hour to 80° C., the ethanol evaporated off, water (100 cc) added and the aqueous phase washed with ethyl ether (3×50 cc). The aqueous phase is acidified to pH 1 and extracted with ethyl ether (5×100 cc). The organic phase is dried over magnesium sulphate, filtered and evaporated to dryness under reduced pressure.

The product (4.8 g) obtained is recrystallized in ethanol, and 2-(2-chlorophenyl)-4-quinazolinepropanoic acid (2.2 g), m.p. 175° C., recovered.

EXAMPLE 11

The procedure is as in Example 7, starting with 2-(4-nitrophenyl)-4-quinazolinepropanoic acid (1.35 g), carbonyldiimidazole (0.82 g) and diethylamine (0.9 cc) in anhydrous tetrahydrofuran (20 cc). After chromatography on silica gel with ethyl acetate as eluant, and recrystallization in ethyl acetate, N,N-diethyl-2-(4-nitrophenyl)-4-quinazolinepropanamide (0.35 g), m.p. 168° C., is obtained.

2-(4-Nitrophenyl)-4-quinazolinepropanoic acid is prepared according to the following process:

A mixture of para-nitrobenzoic acid (3.34 g) and thionyl chloride (20 cc) is brought to reflux for 3 hours. The excess thionyl chloride is removed by evaporation under reduced pressure, and chloroform (20 cc), triethylamine (5.5 cc) and ethyl 3-(2-aminobenzoyl)propionate (2.21 g) are added to the residual product. The mixture is stirred at room temperature (approximately 20° C.) for 2 hours. The solvent is removed under reduced pressure, and the residue taken up in ethyl acetate (50 cc), the mixture is filtered and the filtrate concentrated to dryness. The residue product is placed in contact with ammonium acetate (20 g) and brought to 150° C. for 6 hours. After the mixture is cooled water (250 cc) is added and the mixture is extracted with ethyl acetate (4×100 cc). The organic phase is washed with N sodium hydroxide solution (2×100 cc) and water (50 cc). The organic phase is dried over magnesium sulphate, filtered and evaporated to dryness under reduced pressure. A product (2.8 g) is obtained, and this is placed in contact with ethanol (50 cc) and concentrated sodium hydroxide solution (2.5 cc). After 30 minutes at room temperature, the ethanol is removed by evaporation under reduced pressure and water (200 cc) is added. The aqueous phase is washed with ethyl ether (3×50 cc) and acidified to pH 1, and the precipitate formed is filtered off. After this is washed with water and methylene chloride and dried, 2-(4-nitrophenyl)-4-quinazolinepropanoic acid (1.4 g) is obtained, its proton NMR spectrum in deuterated dimethyl sulphoxide having the following characteristics:

| Ar—$CH_2$ δ: 3.7 ppm | —$CH_2$—COOH δ: 3 ppm |
| --- | --- | aromatic H meta to the $NO_2$ δ: 8.4 ppm
aromatic H ortho to the $NO_2$ δ: 8.9 ppm
other aromatic H from 7.7 to 8.4 ppm.

EXAMPLE 12

The procedure is as in Example 7, starting with 2-(4-methylphenyl)-4-quinazolinepropanoic acid (1.32 g), carbonyldiimidazole (0.88 g) and diethylamine (0.95 cc) in anhydrous tetrahydrofuran (20 cc).

After chromatography on silica gel with ethyl acetate as eluant, and recrystallization in 50% strength aqueous ethanol, N,N-diethyl-2-(4-methylphenyl)-4-quinazolinepropanamide (0.75 g), m.p. 80° C., is obtained.

2-(4-Methylphenyl)-4-quinazolinepropanoic acid is obtained according to the following process:

A mixture of 4-methylbenzoic acid (2.72 g) and thionyl chloride (20 cc) is brought to boiling for 4 hours. The excess thionyl chloride is removed by evaporation under reduced pressure, and ethyl 3-(2-aminobenzoyl)propionate (2.21 g), toluene (20 cc) and triethylamine (5.5 cc) are added to the residue. The mixture is stirred for 1 hour at room temperature (approximately 20° C.) and filtered, and the filtrate is evaporated under reduced pressure. Ammonium acetate (20 g) is added to the residual product, and the mixture is brought to 110° C. for 7 hours. After it is cooled, water (100 cc) is added and the aqueous phase extracted with ethyl acetate (3×100 cc). The solvent is evaporated off under reduced pressure and ethanol (20 cc) and concentrated sodium hydroxide solution (3 cc) are added to the residue. The mixture is brought to 80° C. for 1 hour, the ethanol evaporated off under reduced pressure, water (100 cc) added and the aqueous phase washed with ethyl ether (3×100 cc). The aqueous phase is acidified to pH 1 and the solid extracted with ethyl acetate (3×100 cc). The organic phase is dried over magnesium sulphate, filtered and evaporated to dryness under reduced pressure. The product (3.1 g) obtained is recrystallized in absolute ethanol, and 2-(4-methylphenyl)-4-quinazolinepropanoic acid (1.5 g), m.p. 180° C., recovered.

EXAMPLE 13

The procedure is as in Example 7, starting with 2-(2-pyridyl)-4-quinazolinepropanoic acid (1.34 g), carbonyldiimidazole (0.93 g) and diethylamine (1 cc) in dimethylformamide (25 cc). After chromatography on silica gel with a chloroform/methanol (95:5 by volume) mixture as eluant, and crystallization in ethyl acetate, N,N-diethyl-2-(2-pyridyl)-4-quinazolinepropanamide (0.58 g), m.p. 130° C. is obtained.

2-(2-Pyridyl)-4-quinazolinepropanoic acid is prepared according to the following process:

2-Pyridinecarboxylic acid (2.46 g) and dry dimethylformamide (15 cc) are placed under nitrogen. Carbonyldiimidazole (3.89 g) is added, the mixture is stirred for 20 minutes and a solution of ethyl 3-(2-aminobenzoyl)-propionate (2.21 g) in dry dimethylformamide (10 cc) is added. The mixture is brought to 110° C. for 20 hours and the solvent evaporated off under reduced pressure. Water (50 cc) is added and the mixture is extracted with ethyl ether (4×50 cc).

The organic phase is dried over magnesium sulphate and evaporated to dryness under reduced pressure. The crude product (3.17 g) obtained is recrystallized in absolute ethanol. Ethyl 3-[2-(2-pyridinecarboxamido)benzoyl]-propionate (1.7 g) is obtained and this is placed in contact with ammonium acetate (10 g) and acetic acid (5 cc. The mixture is brought for 10 hours to 110° C. After it is cooled, water (100 cc) is added and the aqueous phase is extracted with ethyl acetate (3×50 cc). The solvent is evaporated off under reduced pressure and the residual product taken up with ethanol (20 cc) and concentrated sodium hydroxide (2 cc). The mixture is brought to 80° C. for 1 hour, the ethanol evaporated off and water (25 cc) added, and acetic acid is added until the pH is 4. The precipitate is filtered off, washed with water and methylene chloride and dried. 2-(2-Pyridyl)-4-quinazolinepropanoic acid (0.82 g) is obtained, the proton NMR spectrum of which, in deuterated chloroform plus deuterated dimethyl sulphoxide, has the following characteristics:

| Ar—$\underline{CH_2}$— | δ: 3.7 ppm | —$\underline{CH_2}$—COOH | δ: 3 ppm |
|---|---|---|---|
| H$_6$ pyridyl | δ: 8.9 ppm | H$_5$ pyridyl | δ: 7.5 ppm |
| | other aromatic H from 7.6 to 8.3 ppm | | |

EXAMPLE 14

The procedure is as in Example 7, starting with α-methyl-3-phenyl-1-isoquinolinepropanoic acid (8 g), carbonyldiimidazole (1.62 g) and diethylamine (5 cc) in tetrahydrofuran (25 cc).

After three chromatographic separations on silica gel with a cyclohexane/ethyl acetate (7:3 by volume) mixture as eluant, and crystallization in isopropyl ether, N,N-diethyl-α-methyl-3-phenyl-1-isoquinolineoropanamide (1.3 g) m.p. 57° C., is obtained. α-Methyl-3-phenyl-1-isoquinolinepropanoic acid is prepared according to the following process:

Sodium hydride (2.1 g, 60% strength in oil) and anhydrous tetrahydrofuran (50 cc) are placed under nitrogen. A solution of diethyl methylmalonate (9.1 g) in anhydrous tetrahydrofuran (50 cc) is added dropwise. Stirring is continued for 1 hour at room temperature (approximately 20° C.) and a solution of 1-bromomethyl-3-phenylisoquinoline (10.4 g) in anhydrous tetrahydrofuran (100 cc) is added. After 20 hours of contact, water (200 cc) is added and the aqueous phase extracted with ethyl acetate (3×50 cc). After removal of the solvents under reduced pressure, the product (19 g) recovered is brought to boiling for 20 hours in concentrated hydrochloric acid (70 cc) and acetic acid (70 cc). After being cooled, the mixture is poured into water (1000 cc) and alkalinised to pH 10 with sodium hydroxide solution, and the aqueous phase is washed with ethyl acetate (100 cc) acidified with hydrochloric acid and extracted with chloroform (3×200 cc). The organic phase is dried over magnesium sulphate, filtered and evaporated to dryness under reduced pressure. α-Methyl-3-phenyl-1isoquinolinepropanoic acid (7.4 g), m.p. 184° C., is obtained.

EXAMPLE 15

2-Phenyl-4-quinolinepropanoic acid (3 g) in thionyl chloride (9 cc) is heated under reflux for 90 minutes. The thionyl chloride is evaporated off, and the residue taken up with toluene (100 cc) and evaporated again. Dry toluene (60 cc) is then added to the residue obtained, and diethylamine (10 cc) is introduced dropwise with stirring in the course of 20 minutes. The mixture is stirred for one hour at room temperature (approximately 20° C.) and taken up with water (60 cc). The organic phase is decanted. The aqueous phase is extracted with toluene (2×30 cc). The organic phases are combined, dried over magnesium sulphate and evaporated under reduced pressure.

The residue obtained is taken up in acetone and, after addition of a solution of hydrochloric acid in ethyl ether, N,N-diethyl-2-phenyl-4-quinolinepropanamide hydrochloride (2.3 g), m.p. 126° C., is isolated.

2-Phenyl-4-quinolinepropanoic acid can be prepared according to J. HANNS, Ber, 58 (B), 2799–2805 (1925).

EXAMPLE 16

2-Phenyl-4-quinolinepropanoic acid (5 g) and thionyl chloride (1.43 cc) in chloroform (250 cc) are heated under reflux overnight. The procedure is then as in Example 15, but using piperidine (5.3 cc).

The residue is stirred for one hour with silica gel (60 g) in ethyl acetate (100 cc). The silicate is removed by filtration and washed with ethyl acetate (7×10 cc). The organic phases are combined and evaporated under reduced pressure. After recrystallization of the residue in ethyl acetate, 1-[3-(2-phenyl-4-quinolyl)propionyl]-piperidine (2 g), m.p. 110° C., is obtained.

EXAMPLE 17

The procedure is as in Example 16, starting with 2-phenyl-4-quinolinepropanoic acid (3 g), thionyl chloride (0.9 cc) in chloroform (150 cc) and morpholine (2.78 cc).

The residue is stirred for one hour with silica gel (35 g) in ethyl acetate (70 cc). The silica is removed by filtration and washed with ethyl acetate (7×10 cc). The organic phases are combined and evaporated under reduced pressure. After recrystallization of the residue in ethyl acetate in the presence of animal charcoal, 4-[3-(2-phenyl-4-quinolyl)propionyl]morpholine (1.5 g), m.p. 140° C., is obtained.

EXAMPLE 18

The procedure is as in Example 16, starting with 2-phenyl-4-quinolinepropanoic acid (3 g), thionyl chloride (2.3 cc) in chloroform (150 cc) and dipropylamine (4.4 cc). The residue is stirred for one hour with silica gel (40 g) in ethyl acetate (80 cc). The silica is removed by filtration and washed with ethyl acetate (7×10 cc). The organic phases are combined and evaporated under reduced pressure.

The residue obtained is taken up with acetone and, after addition of a solution of hydrochloric acid in ethyl ether, N,N-dipropyl-2-phenyl-4-quinolinepropanamide hydrochloride (2.41 g), m.p. 130° C., is isolated.

EXAMPLE 19

The procedure is as in Example 16, starting with 2-phenyl-4-quinolinepropanoic acid (3 g), thionyl chloride (2.3 cc) in chloroform (150 cc) and pyrrolidine (2.7 cc). The residue is stirred for two hours with silica gel (36 g) in ethyl acetate (80 cc). The silica is removed by filtration and washed with ethyl acetate (7×10 cc). The organic phases are combined and concentrated under reduced pressure. After recrystallization of the residue in ethyl acetate, 1-[3-(2-phenyl-4-quinolyl)propionyl]-pyrrolidine (2 g), m.p. 116° C., is obtained.

EXAMPLE 20

The procedure is as in Example 16, starting with α-methyl-2-phenyl-4-quinolinepropanoic acid (3 g) in chloroform (30 cc), thionyl chloride (0.97 cc) and diethylamine (3.2 cc) in chloroform (5 cc), and reducing to 30 minutes the preparation time of the acid chloride. The isolated residue is taken up in ethanol and, after addition of a solution of hydrochloric acid in ethyl ether and recrystallization in an ethanol/ethyl ether (1:3 by volume) mixture, N,N-diethyl- α-methyl-2-phenyl-4-quinolinepropanamide hydrochloride (2.9 g), m.p. 161° C., is isolated.

α-Methyl-2-phenyl-4-quinolinepropanoic acid can be prepared according to the following process:

1—Preparation of 4-chloromethyl-2-phenylquinoline.

Thionyl chloride (35 cc) is added in the course of 45 minutes to a suspension, cooled to 10° C., of 2-phenyl-4-quinolinemethanol (45 g) in chloroform (450 cc), and the mixture is then stirred for 4 hours at room temperature (approximately 20° C.). The solvent is evaporated off under reduced pressure, the residue taken up several times with toluene and the toluene evaporated off so as to remove the thionyl chloride.

The residue is taken up with water (1000 cc), and alkalinised to pH 9 by adding concentrated ammonium hydroxide solution. The aqueous phase is extracted with ethyl ether (3×500 cc), and the ether phase is washed with water (3×200 cc), dried over magnesium sulphate and evaporated under reduced pressure. The oily residue is taken up in isopropyl ether, and the ether is then evaporated under reduced pressure. 4-Chloromethyl-2-phenylquinoline (45.3 g), m.p. 79° C., is thereby obtained.

2-Phenyl-4-quinolinemethanol can be prepared according to ROSENMUND and ZYMALKOVSKI, B, 85, 152–159 (1952).

2—Preparation of α-methyl-2-phenyl-4-quinoline propionic acid.

Sodium hydride (14.3 g, 60% strength dispersion in oil) is added slowly under an atmosphere of nitrogen to dry tetrahydrofuran (220 cc). A solution of diethyl methylmalonate (62.5 g) in tetrahydrofuran (220 cc) is then introduced slowly in the course of 2 hours, followed by a solution of 4-chloromethyl-2-phenylquinoline (45.3 g) in tetrahydrofuran (400 cc) in the course of one hour, the mixture is stirred for two hours at room temperature (approximately 20° C.) and then heated for 1 hour 30 minutes under reflux. The mixture is brought back to room temperature (approximately 20° C.) and glacial acetic acid (22 cc) is added dropwise, followed by water (500 cc). The tetrahydrofuran is removed by evaporation under reduced pressure; the reaction medium is diluted with water (500 cc) and extracted with ethyl ether (3×400 cc). The ether phase is washed with water and concentrated under reduced pressure.

The residue obtained is taken up with concentrated hydrochloric acid solution (500 cc) and glacial acetic acid (500 cc). The mixture is heated for 3 hours 30 minutes under reflux. The acids are evaporated off as completely as possible under reduced pressure, the residue is taken up with water (1000 cc) and alkalinised to pH 10 by adding concentrated ammonium hydroxide solution, ethyl ether (300 cc) is added and the mixture is left for 15 minutes with stirring. The organic phase is decanted and washed with water (2×200 cc). The aqueous phase is washed with ethyl ether (2×300 cc). The aqueous phases are combined and acidified with stirring to pH 4-5 using glacial acetic acid, the mixture is stirred for a further hour, the precipitate is then drained and α-methyl-2-phenyl-4-quinolinepropanoic acid (47.6 g), m.p. 211° C., is obtained.

EXAMPLE 21

The procedure is as in Example 20, starting with laevorotatory α-methyl-2-phenyl-4-quinolinepropanoic acid (3 g) in chloroform (30 cc), thionyl chloride (0.97 cc) and diethylamine (3.2 cc) in chloroform (5 cc).

The isolated residue is taken up in ethanol and, after addition of a solution of hydrochloric acid in ethyl ether and recrystallization in an ethanol/ethyl ether (1:3 by volume) mixture followed by two recrystallizations in an ethanol/ethyl ether (1:2 by volume) mixture, laevorotatory N,N-diethyl-α-methyl-2-phenyl-4-quinolinepropanamide hydrochloride (2 g), m.p. 175° C., is isolated.

$\alpha_D$ at 0.5% in EtOH at 21° C. = −85.5°±2°.

Laevorotatory α-methyl-2-phenyl-4-quinolinepropanoic acid can be prepared by resolution of racemic α-methyl-2-phenyl-4-quinolinepropanoic acid, working in the following manner:

(1) Preparation of the diastereoisomeric N-(1-phenyl-2-hydroxyethyl)-α-methyl-2-phenyl-4-quinolinepropanamides.

α-Methyl-2-phenyl-4-quinolinepropanoic acid (42.5 g) and thionyl chloride (13.8 cc) in chloroform (450 cc) are heated under reflux for one hour. The solvent is evaporated off under reduced pressure, and the residue taken up with chloroform which is evaporated off again.

Triethylamine (41 cc) is added to a stirred solution of (−)-α-phenylglycinol (20 g) in chloroform (200 cc), and a solution in chloroform (400 cc) of the acid chloride prepared above is then introduced in the course of 1 hour 30 minutes. The mixture is stirred for two hours at room temperature (aoproximately 20° C.), the chloroform evaporated off under reduced pressure and the residue taken up with water (500 cc) and ethyl acetate (300 cc). The organic phase is decanted and the aqueous phase extracted with ethyl acetate (100 cc). The organic phases are combined, washed with water, dried over magnesium sulphate and evaporated under reduced pressure. The residue obtained (10 g) is chromatographed on silica gel using a chloroform/ethyl acetate (50:50 by volume) mixture as eluant.

N-(1-Phenyl-2-hydroxyethyl)-α-methyl-2-phenyl-4-quinolinepropanamide, A form (4.6 g), m.p. 134° C., which is eluted first, and then N-(1-phenyl-2-hydroxyethyl)-α-methyl-2-phenyl-4-quinolinepropanamide, B form (4.6 g), which is eluted subsequently and which has an m.p. of 158° C., are thereby obtained.

(2) Preparation of laevorotatory-α-methyl-2-phenyl-4-quinolinepropanoic acid.

N-(1-Phenyl-2-hydroxyethyl)-α-methyl-2-phenyl-4quinolinepropanamide, A form (5.5 g) in glacial acetic acid (27 cc) and concentrated hydrochloric acid solution (27 cc) is heated under reflux for 1 hour 30 minutes.

The acids are then evaporated under reduced pressure, the residue is taken up with water (120 cc) and alkalinised to pH 10 by means of concentrated ammonium hydroxide solution, and the aqueous phase is washed with ethyl ether (250 cc). The aqueous phase is acidified to pH 5 with glacial acetic acid and extracted with ethyl acetate (3×100 cc). The organic phase is washed with water, dried over magnesium sulphate and concentrated under reduced pressure.

After recrystallization in ethanol, laevorotatory α-methyl-2-phenyl-4-quinolinepropanoic acid (2.6 g), m.p. 185° C., is obtained. $\alpha_D$ at 0.5% in glacial acetic acid = $-37.7° \pm 2°$ at 22° C.

EXAMPLE 22

The procedure is as in Example 20, starting with dextrorotatory-α-methyl-2-phenyl-4-quinolinepropanoic acid (3.4 g) in chloroform (34 cc), thionyl chloride (1.1 cc) and diethylamine (3.6 cc) in chloroform (5 cc). The isolated residue is taken up in ethanol and, after addition of a solution of hydrochloric acid in ethyl ether, recrystallization in an ethanol/ethyl ether (1:3 by volume) mixture followed by a further crystallization in an ethanol/ethyl ether (1:2 by volume) mixture, dextrorotatory N,N-diethyl-α-methyl-2-phenyl-4-quinolinepropanamide hydrochloride (2.55 g), m.p. 175° C., is isolated.

$\alpha_D$ at 0.5% in EtOH at 21° C. = $+81.6° \pm 2°$.

Dextrorotatory-α-methyl-2-phenyl-4-quinolinepropanoic acid can be prepared like its laevorotatory enantiomer described in Example 21, starting with N-(1-phenyl-2-hydroxyethyl)-α-methyl-2-phenyl-4-quinolinepropanamide, B form (6.6 g), prepared according to Example 21, concentrated hydrochloric acid solution (33 cc) and acetic acid (33 cc).

The residue obtained is recrystallized in ethanol.

Dextrarotatory α-methyl-2-phenyl-4-quinolinepropanoic acid (3.9 g), m.p. 186° C., is obtained.

$\alpha_D$ at 0.5% in glacial acetic acid at 24° C. = $+33.3° \pm 2°$.

EXAMPLE 23

The procedure is as in Example 20, starting with α-methyl-2-phenyl-4-quinolinepropanoic acid (2.03 g) in chloroform (20 cc), thionyl chloride (0.67 cc) and a 3 M solution (7 cc) of dimethylamine in toluene. The residue is taken up in ethanol and, after addition of a solution of hydrochloric acid in ethyl ether and recrystallization in an ethanol/ethyl ether (1:2 by volume) mixture, N,N-dimethyl-α-methyl-2-phenyl-4-quinolinepropanamide hydrochloride (1.4 g), m.p. 160° C., is isolated.

EXAMPLE 24

Thionyl chloride (1.02 cc) is added to a solution of 2-phenyl-4-quinolinebutanoic acid (3.7 g) in chloroform (60 cc), and the mixture is heated under reflux for 15 minutes. The solvents are evaporated off under reduced pressure. The residue obtained is dissolved in chloroform (40 cc). Diethylamine (6 cc) is added slowly to this solution in the course of 20 minutes. The mixture is stirred for 3 hours at room temperature (approximately 20° C.) and taken up with water (40 cc). The organic phase is decanted, washed with water (40 cc), dried over magnesium sulphate and evaporated under reduced pressure. The residue is chromatographed on silica gel, using a cyclohexane/ethyl acetate (50:50 by volume) mixture as eluant. N,N-Diethyl-2-phenyl-4-quinolinebutanamide (3.3 g) is thereby obtained, and this is converted to the monohydrochloride in acetone. The hydrochloride melts at 130° C.

2-Phenyl-4-quinolinebutanoic acid can be prepared in the following manner:

1-Preparation of ethyl γ-oxo-2-phenyl-4-quinolinebutanoate.

A 20% strength suspension (84 cc) of potassium hydride in oil is added slowly to dry tetrahydrofuran (500 cc) under an atmosphere of nitrogen. Ethyl 2-phenyl-4-quinolinecarboxylate (47 g) is then introduced with stirring, and a solution of ethyl succinate (24.4 g) in tetrahydrofuran (250 cc) is then added slowly in the course of 2 hours at room temperature (approximately 20° C.). Ethanol (80 cc) is then added, followed by water (800 cc). The tetrahydrofuran is removed by evaporation, and the aqueous phase is extracted with ethyl ether (2×200 cc), then acidified to pH 4.5 by adding glacial acetic acid and finally extracted with ethyl ether (3×200 cc). The ether phase is washed with water, dried over magnesium sulphate and evaporated under reduced pressure.

The residue is taken up with 6 N hydrochloric acid solution (600 cc), and the mixture is heated under reflux for 6 hours. After concentration under reduced pressure, a mixture (57.4 g) containing 2-phenyl-4-quinolinecarboxylic acid and γ-oxo-2-phenyl-4-quinolinebutanoic acid is obtained.

This mixture is taken up with absolute ethanol (600 cc) and concentrated sulphuric acid (60 cc) and heated under reflux overnight. The ethanol is removed by evaporation under reduced pressure, and the residue is poured into ice-cold water (600 cc) and concentrated ammonium hydroxide solution (220 cc). This aqueous phase is extracted with ethyl ether (3×700 cc), and the organic phase is washed with water, dried over magnesium sulphate and evaporated under reduced pressure. The residue is chromatographed on silica gel using a cyclohexane/ethyl acetate (90:10 by volume) mixture as eluant. Ethyl γ-oxo-2-phenyl-4-quinolinebutanoate (24.4 g), m.p. 66° C., is thereby obtained.

2-Preparation of 2-phenyl-4-quinolinebutanoic acid.

A mixture of ethyl γ-oxo-2-phenyl-4-quinolinebutanoate (5 g) and 98% pure hydrazine hydrate (2.25 cc) in diethylene glycol (15 cc) is heated to 150° C. for 15 minutes. The mixture is cooled to 120° C., potassium hydroxide pellets (2.5 g) are then introduced in the course of 15 minutes and the mixture is heated to 150° C. for 1 hour 30 minutes.

The reaction mixture is diluted with water (300 cc) and extracted with ethyl ether (3×80 cc). The ether phase is washed with water (10 cc), and the aqueous phases are combined, acidified to pH 4.5 by adding acetic acid and extracted with ethyl ether 3×100 cc). The ether phase is washed with water, dried over magnesium sulphate and evaporated under reduced pressure. 2-Phenyl-4-quinolinebutanoic acid (3.7 g), m.p. 125° C., is obtained.

EXAMPLE 25

The procedure is as in Example 24, starting with α-ethyl-2-phenyl-4-quinolinebutanoic acid hydrochloride (1.7 g) in chloroform (35 cc), thionyl chloride (0.38 cc) and diethylamine (2.2 cc). After chromatography of the residue on silica gel, using a cyclohexane/ethyl acetate (80:20 by volume) mixture as eluant and crystallization in 40–60° petroleum ether, N,N-diethyl-α-ethyl-2-phenyl-4-quinolinebutanamide (1.1 g), m.p. 81° C., is obtained.

α-Ethyl-2-phenyl-4-quinolinebutanoic acid is prepared by hydrolysis of the corresponding ethyl ester by means of 6 N hydrochloric acid solution.

Ethyl α-ethyl-2-phenyl-4-quinolinebutanoate is prepared in the following manner:

Diisopropylamine (2.96 cc) is added to dry tetrahydrofuran (30 cc) placed under an atmosphere of nitrogen. The solution is stirred and cooled to −70° C. A 1.6 M solution (11.3 cc) of butyllithium in hexane is then introduced in the course of 15 minutes, and then, after stabilization of the temperature at −70° C., a solution of ethyl 2-phenyl-4-quinolinebutanoate (3.8 g) in tetrahydrofuran (30 cc) is introduced in the course of 5 minutes. The mixture is stirred for 30 minutes at −70° C. and ethyl iodide (1.15 cc) and hexamethylphosphoramide (0.8 cc) in tetrahydrofuran (20 cc) are introduced in the course of 5 minutes. The mixture is stirred for 7 hours at −70° C. Ethanol (7 cc) is added followed by acetic acid (2 cc). The temperature is allowed to rise to room temperature (approximately 20° C.), and the reaction medium is diluted with water (300 cc) and extracted with ethyl ether (2×100 cc). The ether phase is washed with water, dried over magnesium sulphate and evaporated under reduced pressure. The residue is chromatographed on silica gel using a cyclohexane/ethyl acetate (90:10 by volume) mixture. Ethyl α-ethyl-2-phenyl-4-quinolinebutanoate (1.8 g), m.p. 76° C., is thereby isolated.

Ethyl 2-phenyl-4-quinolinebutanoate can be prepared by esterification of the corresponding acid, the preparation of which is described in Example 24, using ethanol in the presence of sulphuric acid.

EXAMPLE 26

The procedure is as in Example 24, starting with 2-phenyl-5-quinolinepentanoic acid (4 g) in chloroform (80 cc), thionyl chloride (1.05 cc) and diethylamine (6 cc).

The residue obtained is chromatographed on silica gel using a cyclohexane/ethyl acetate (50:50 by volume) mixture as eluant. N,N-Diethyl-2-phenyl-4-quinolinepentanamide (2.7 g) is thereby isolated in the form of a yellow oil. The proton NMR spectrum in deuterated chloroform shows the following characteristics:

| Ar—CH$_2$—CH$_2$ | δ: 3.13 ppm |
|---|---|
| —CH$_2$—CON | δ: 2.32 ppm |
| H$_3$ | δ: 7.68 ppm |
| Ar—CH$_2$—CH$_2$—CH$_2$—CH$_2$—CON | δ: 1.84 ppm |

2-Phenyl-5-quinolinepentanoic acid can be prepared according to the following process:

(1) Preparation of δ-oxo-2-phenyl-4-quinolinepentanoic acid.

A solution of ethyl γ-oxo-2-phenyl-4-quinol inepropionate (prepared according to F. GES, Chim. Ind. Basel, DRP 462,136) in toluene (50 cc) is added at 100° C. in the course of 5 minutes to a suspension of sodium ethylate [prepared from sodium (0.92 g) and ethanol (2.34 cc)] in toluene (200 cc). The mixture is heated for one hour to 100° C. and ethyl acrylate (4.4 cc) is then added; the mixture is heated for 3 hours 30 minutes to 100° C., ethyl acetate (2.2 cc) is added and the mixture is stirred at 100° C. overnight. The mixture is brought back to room temperature (approximately 20° C.), and acetic acid (35 cc) is added, followed by water (150 cc) and ethyl ether (50 cc).

The organic phase is decanted, washed with water, dried over magnesium sulphate and evaporated under reduced pressure. The residue is chromatographed on silica gel using a cyclohexane/ethyl acetate (90:10 by volume) mixture as eluant. The β-keto ester (6.6 g) thereby obtained is taken up with 6 N hydrochloric acid solution (130 cc) and heated under reflux for one hour. The mixture is cooled to 0° C., alkalinised to pH 9 adding concentrated ammonium hydroxide solution (60 cc), and then acidified to pH 4 by adding glacial acetic acid.

The aqueous phase is extracted with ethyl ether (3×150 cc) and the organic phase is dried over magnesium sulphate and evaporated under reduced pressure. δ-Oxo-2-phenyl-4-quinolinepentanoic acid (4.7 g), m.p. 136° C., is thereby obtained.

(2) Preparation of 2-phenyl-4-quinolinepentanoic acid.

The procedure is the same as that used for preparing 2-phenyl-4-quinolinebutanoic acid described in Example 24, but starting with δ-oxo-2-phenyl-4-quinolinepentanoic acid (4.6 g), 98% pure hydrazine hydrate (2.15 g), potassium hydroxide pellets (2.4 g) and diethylene glycol (14 cc). 2-Phenyl-4-quinolinepentanoic acid (4 g) is thereby isolated, its proton NMR spectrum in deuterated chloroform showing the following characteristics:

| Ar—CH$_2$ | δ: 3.16 ppm |
|---|---|
| Ar—CH$_2$—CH$_2$—CH$_2$—CH$_2$—COOH | δ: 1.83 ppm |
| CH$_2$—COOH | δ: 2.37 ppm |
| H$_3$ | δ: 7.59 ppm |

EXAMPLE 27

Triethlamine (3.78 cc) is added to a suspension of 2-phenyl-4-quinolinepropanoic acid (2.5 g) in chloroform (100 cc), followed, under nitrogen and after the mixture has been cooled to 10° C., by ethylchloroformate (1.24 g). The mixture is then stirred for 40 minutes at room temperature (approximately 20° C.), and N-methyl-2-butanamine hydrochloride (1.05 g) is then introduced in small portions. The mixture is stirred for 20 hours at room temperature (approximately 20° C.). After evaporation of the solvent under reduced pressure, the residue is taken up in ethyl acetate, and the organic phase is washed with saturated aqueous sodium carbonate solution and dried over magnesium sulphate. The residue obtained after evaporation of the solvent under reduced pressure is chromatographed under pressure on silica gel, initially with a cyclohexane/toluene/diethylamine (80:15:5 by volume) mixture, a second time with a cyclohexane/toluene/diethylamine (90: 7.5:2.5 by volume) mixture, and a third time with a hexane/ethyl acetate (50:50 by volume) mixture. The residue obtained is taken up in acetone and, after addition of a solution of hydrochloric acid in ethyl ether, the product is isolated in the form of the crude hydrochloride. The latter is recrystallized in an isopropanol/isopropyl ether mixture. After a return to the base using 2 N sodium hydroxide, extraction with ethyl acetate and evaporation under reduced pressure, N-methyl-N-(1-methylpropyl)-2-phenyl-4-quinolinepropanamide (0.45 g) is isolated in the form of an oil, the proton NMR spectrum of which in deuterated chloroform shows the following characteristics:

| Ar—CH$_2$—CH$_2$ | δ: 3.52 ppm | N—CH$_3$ | δ: 2.65–2.78 ppm |
| —CH$_2$—CO—N | δ: 2.78 ppm | H$_3$ | δ: 7.73 ppm |

EXAMPLE 28

Meta-trifluoromethylbenzoic acid (1.71 g) and thionyl chloride (20 cc) are brought to reflux for 20 hours. The excess thionyl chloride is evaporated off under reduced pressure and the residue taken up in chloroform (20 cc) and triethylamine (1.9 cc), and N,N-diethyl-3-(2-aminobenzoyl)propanamide (1.11 g) is added. After 1 hour's contact at room temperature (approximately 20° C.), the chloroform is evaporated off under reduced pressure and the residual product taken up in ethyl ether, the mixture is filtered and the filtrate evaporated to dryness. The residue is mixed with acetic acid (5 cc) and ammonium acetate (5 g) and the mixture is brought to 100° C. for 6 hours. The acetic acid is evaporated off under reduced pressure, water (50 cc) is added and the mixture is extracted with ethyl acetate (3×50 cc). The organic phase is dried over magnesium sulphate and evaporated to dryness under reduced pressure. The crude product is chromatographed on silica gel with a cyclohexane/ethyl acetate (1:1 by volume) mixture as eluant. The product (1.2 g) is recovered and crystallized in isopropyl ether. N,N-Diethyl-2-(3-trifluoromethylphenyl)-4-quinazolinepropanamide (0.75 g), m.p. 115° C., is obtained.

N,N-Diethyl-3-(2-aminobenzoyl)propanamide is prepared according to the following process:

Cuprous chloride (0.5 g) and pyridine (1.22 cc) in methylene chloride (20 cc) are placed in a gentle stream of air. After 15 minutes, a solution of N,N-diethyl-3-indolepropanamide in methylene chloride (30 cc) is added dropwise and the mixture is left for 20 hours with stirring and in a stream of air.

The organic solution is washed with saturated ammonium chloride solution (50 cc) and the organic phase is dried over magnesium sulphate and evaporated to dryness under reduced pressure. The residue is taken up in ethanol (40 cc) and 5 N sodium hydroxide solution (10 cc). The mixture is stirred at room temperature (approximately 20° C.) for 1 hour, water (100 cc) is added and the aqueous phase is extracted with ethyl ether (3×100 cc). The ether is evaporated off under reduced pressure and the residual product chromatographed on silica gel with ethyl acetate as eluant. N,N-Diethyl-3-(2-aminobenzoyl)propanamide (2.22 g) is obtained in the form of an oil, the proton NMR spectrum of which in deuterated chloroform has the following characteristics:

| CH$_2$—CH$_3$ | δ: 1.1 and 1.3 ppm |
| —CH$_2$—CO— | δ: 2.8 ppm |
| N—CH$_2$— | δ: 3.3 ppm |
| Aromatic H$_6$ | δ: 7.9 ppm |
| Ar—CO—CH$_2$ | δ: 3.3 ppm |
| H$_4$ | δ: 7.3 ppm |
| H$_3$ and H$_5$ | δ: 6.7 ppm |

N,N-Diethyl-3-indolepropanamide can be prepared according to H. E. JOHNSON et al., J. Org. Chem., 28, 2030 (1963).

EXAMPLE 29

The procedure is as in Example 28, starting with 2-thienoic acid (1.15 g) and thionyl chloride (10 cc), then triethylamine (1.9 cc), N,N-diethyl-3-(2-aminobenzoyl)propanamide (1.11 g) and chloroform (20 cc), and finally ammonium acetate (5 g) and acetic acid (5 cc). After chromatography on silica gel with a cyclohexane/ethyl acetate (1:1 by volume) mixture as eluant and crystallization in isopropyl ether, N,N-diethyl-2-thienyl-4-quinazolinepropanamide (0.83 g), m.p. 106° C., is obtained.

EXAMPLE 30

The procedure is as in Example 28, starting with N,N-diethyl-3-(2-amino-5-bromobenzoyl)propanamide (1.72 g), benzoyl chloride (1.98 g), triethylamine (4.2 cc) and chloroform (20 cc), and then ammonium acetate (5 g) and acetic acid (5 cc).

After chromatography on silica gel with a cyclohexane/ethyl acetate (1:1 by volume) mixture as eluant and recrystallization in ethyl acetate, N,N-diethyl-6-bromo-2-phenyl-4-quinazolinepropanamide (1.32 g), m.p. 146° C., is obtained.

N,N-Diethyl-3-(2-amino-5-bromobenzoyl)propanamide is prepared according to the following process:

5-Bromoindole (13.7 g) and acrylic acid (15 cc) in acetic acid (10 cc) and acetic anhydride (10 cc) are stirred for 72 hours at room temperature (approximately 20° C.).

The solvents are removed under reduced pressure and the residue is chromatographed on silica gel, first with chloroform and then with a chloroform/methanol (98:2 by volume) mixture as eluants. The product (13 g) recovered is taken up, under nitrogen, in dry tetrahydrofuran (60 cc). Carbonyldiimidazole (12.5 g) is added and the mixture is stirred for 1 hour. Diethylamine (15 cc) is then added and the reagents are left in contact for 20 hours. The solvent is removed under reduced pressure, water (100 cc) is added and the mixture is extracted with ethyl acetate (2×100 cc) and then ethyl ether (2×100 cc). The organic phase is dried over magnesium sulphate, filtered and evaporated to dryness under reduced pressure. The residue is crystallized in ethyl ether, and N,N-diethyl-5-bromo-3-indolepropanamide (7.8 g), m.p. 128° C., is obtained.

Cuprous chloride (0.5 g), pyridine (1.22 cc) and methylene chloride (30 cc) are placed in a stream of air. A solution of N,N-diethyl-5-bromo-3-indolepropanamide (7.5 g) in methylene chloride (60 cc) are then added, the mixture is stirred for 24 hours, cuprous chloride (0.5 g) and pyridine (1.5 cc) are added again and the mixture is stirred for a further 24 hours. Silica (10 g) is added, the mixture is filtered and the filtrate evaporated to dryness under reduced pressure.

The residual product is taken up in ethanol (50 cc), water (5 cc) and concentrated sodium hydroxide solution (5 cc). The mixture is brought to 80° C. for 15 minutes, the ethanol removed by evaporation under reduced pressure, water (50 cc) is added and the aqueous phase is extracted with ethyl ether (3×100 cc). The organic phase is dried over magnesium sulphate and evaporated to dryness under reduced pressure. The residual product is chromatographed on silica gel with a cyclohexane/ethyl acetate (1:1 by volume) mixture and then ethyl acetate. N,N-Diethyl-3-(2-amino-5-bromobenzoyl)propanamide (1.93 g), m.p. 120° C., is recovered.

EXAMPLE 31

The procedure is as in Example 28, starting with N,N-diethyl-3-(2-amino-5-methoxybenzoyl)propanamide (1.5 g), benzoyl chloride (1.9 g), triethylamine (2.7 g) and chloroform (20 cc); and then ammonium acetate (5 g) and acetic acid (5 cc).

After chromatography on silica gel with ethyl acetate as eluant and crystallization in isopropyl ether, N,N-diethyl-6-methoxy-2-phenyl-4-quinazolinepropanamide (0.64 g), m.p. 144° C., is obtained.

N,N-Diethyl-3-(2-amino-5-methoxybenzoyl)-propanamide is prepared according to the following process:

5-Methoxyindole (11.2 g) and acrylic acid (16.4 g) in acetic acid (11 cc) and acetic anhydride (11 cc) are stirred for 72 hours at room temperature (approximately 20° C.).

The solvent is evaporated off under reduced pressure, the residue taken up in normal sodium hydroxide solution (200 cc), the mixture is stirred and filtered and the insoluble product washed with normal sodium hydroxide solution (100 cc). The aqueous phase is acidified to pH 1 and the insoluble material extracted with chloroform (3×100 cc). The organic phase is dried over magnesium sulphate, filtered and evaporated to dryness under reduced pressure. The residual product is chromatographed on silica gel with a chloroform/methanol (95:5 by volume) mixture as eluant, and 5-methoxy-3-indolepropanoic acid (4.6 g) m.p. 128° C., is obtained.

5-Methoxy-3-indolepropanoic acid (8 g) in dry tetrahydrofuran (40 cc) is placed under nitrogen. Carbonyldiimidazole (7.1 g) is added gradually and the mixture is left with stirring for 1 hour at room temperature (approximately 20° C.). Diethylamine (13.4 g) is added and stirring is continued for 2 hours. Water (200 cc) is added and the mixture is extracted with ethyl acetate (3×100 cc). The organic phase is dried over magnesium sulphate, filtered and evaporated to dryness under reduced pressure. The residual product is crystallized with ethyl ether, and N,N-diethyl-5-methoxy-3-indolepropanamide (8 g), m.p. 80° C., is obtained.

Cuprous chloride (1 g), pyridine (2.5 cc) and methylene chloride (60 cc) are placed under a stream of air. After 15 minutes, N,N-diethyl-5-methoxy-3-indolepropanamide (7.7 g) dissolved in methylene chloride (60 cc) is added and the mixture is stirred for 20 hours at room temperature (approximately 20° C.). Silica (10 g) is added, the mixture is stirred and filtered and the filtrate is evaporated under reduced pressure.

The residual product is chromatographed on silica gel with a cyclohexane/ethyl acetate (1:1 by volume) mixture and then with ethyl acetate as eluant. The product (3.8 g) recovered is treated at 80° C. for 30 minutes with ethanol (25 cc), water (2.5 cc) and concentrated sodium hydroxide solution (2.5 cc). The ethanol is evaporated off under reduced pressure, water (100 cc) is added and the mixture is extracted with ethyl ether (3×50 cc). The organic phase is dried over magnesium sulphate, filtered and evaporated to dryness under reduced pressure. N,N- Diethyl-3-(2-amino-5-methoxybenzoyl)propanamide (1.5 g) is obtained in the form of an oil, which is used as it is.

EXAMPLE 32

The procedure is as in Example 28, starting with N,N-diethyl-3-(2-amino-3-methylbenzoyl)propanamide (2.62 g), benzoyl chloride (2.5 cc), triethylamine (6.6 cc) in chloroform (30 cc) and then ammonium acetate (10 g) and acetic acid (10 cc).

After chromatography on silica gel with a cyclohexane/ethyl acetate (1.1 by volume) mixture as eluant and crystallization in isopropyl ether, N,N-diethyl-8-methyl-2-phenyl-4-quinazolinepropanamide (1.95 g), m.p. 80° C., is obtained.

N,N-Diethyl-3-(2-amino-3-methylbenzoyl)propanamide is prepared according to the following process:

7-Methylindole (26.2 g) is stirred for 48 hours at room temperature (approximately 20° C.) with acrylic acid (30 cc) in acetic anhydride (10 cc) and acetic acid (20 cc). The solvents are evaporated off and the residual product is chromatographed on silica gel with chloroform as eluant.

7-Methyl-3-indolepropanoic acid (14 g), m.p. 110° C., is recovered.

7-Methyl-3-indolepropanoic acid (17 g) and dry tetrahydrofuran (100 cc) are placed under nitrogen. Carbonyldiimidazole (17.2 g) is added gradually, the mixture is left with stirring for 1 hour, diethylamine (45 cc) is added and the mixture is stirred for a further 2 hours. Water (300 cc) is added and the mixture is extracted with ethyl acetate (300 cc, and then 2×100 cc). The organic phase is dried over magnesium sulphate, filtered and evaporated to dryness under reduced pressure. The residual product is taken up in ethyl ether (100 cc) and, after filtration and drying, N,N-diethyl-7-methyl-3-indolepropanamide (18.8 g) is recovered and redissolved in methanol (350 cc). A solution of sodium metaperiodate (47 g) in water (250 cc) is added and the mixture is stirred for 24 hours. The mixture is filtered and the filtrate diluted with water (250 cc) and extracted with methylene chloride (3×250 cc). The organic phase is dried over magnesium sulphate, filtered and evaporated to dryness under reduced pressure. The residual product is taken up in ethanol (200 cc) and concentrated hydrochloric acid (20 cc). The reagents are left in contact for 72 hours at room temperature (approximately 20° C.), the ethanol is evaporated off under reduced pressure, water (200 cc) is added, and the aqueous phase is washed with ethyl ether, alkalinised to pH 11 and extracted with ethyl ether (2×100 cc). The organic phase is dried over magnesium sulphate, filtered and evaporated to dryness under reduced pressure.

The residual solid is recrystallized in a mixture of ethyl acetate (20 cc) and isopropyl ether (50 cc). N,N-

Diethyl-3-2-amino-3-methylbenzoyl)propanamide (6.7 g), m.p. 104° C., is obtained.

EXAMPLE 33

To a stirred suspension of 2-phenyl-4-quinolinol (2.21 g) in dimethylformamide (15 cc), triethylamine (2.1 cc) is added under nitrogen, followed by N,N-diethylcarbamoyl chloride (2.03 g). The reaction mixture is heated to 70° C. for 13 hours, and then poured into ice-cold water (400 cc) and chloroform (400 cc). The insoluble material is removed by filtration, and the organic phase is washed with water, dried over magnesium sulphate and evaporated under reduced pressure. The residue is converted in ethyl ether to a crude hydrochloride (1.6 g) which is taken up with water (200 cc) and concentrated sodium hydroxide solution (5 cc); this alkaline phase is extracted with ethyl ether (2×100 cc) The ether phase is washed with water (6×50 cc), dried over magnesium sulphate and evaporated under reduced pressure.

The residue obtained is taken up in ethyl ether and, after addition of a solution of hydrochloric acid in ethyl ether, 2-phenyl-4-quinolyl N,N-diethylcarbamate hydrochloride (1.28 g), m.p. 120° C., is isolated.

2-Phenyl-4-quinolinol can be prepared according to C. HAUSER and A. REYNOLDS, J.A.C.S., 70, 2402-04 (1948).

EXAMPLE 34

The procedure is as in Example 33, but starting with 2-phenyl-4-quinolinol (4.42 g), triethylamine (4.2 cc) and 1-(chlorocarbonyl)piperidine (4.42 g) in dimethylformamide (30 cc). The residue obtained is purified as in Example 33 and taken up in ethyl ether, and after addition of a solution of hydrochloric acid in ethyl ether, 2-phenyl-4-quinolyl 1-piperidinecarboxylate hydrochloride (2.56 g), m.p. 120° C., is isolated.

EXAMPLE 35

The procedure is as in Example 33, but starting with 4-phenyl-2-quinolinol (2.47 g), triethylamine (2.33 cc) and 1-(chlorocarbonyl)piperidine (2.47 g) in dimethylformamide (30 cc). The residue obtained is purified by chromatography on silica gel using a cyclohexane/ethyl acetate (80:20 by volume) eluant. 4-Phenyl-2-quinolyl 1-piperidinecarboxylate (0.51 g), m.p. 85° C., is thereby isolated.

4-Phenyl-2-quinolinol can be prepared according to C. HAUSER and A. REYNOLDS, J.A.C.S, 70, 2402-04 (1948).

EXAMPLE 36

The procedure is as in Example 33, but starting with 4-phenyl-2-quinolinol (3.54 g), N,N-diethylcarbamoyl chloride (2.2 g) and triethylamine (3.36 cc) in dimethylformamide (60 cc).

The residue obtained is purified by chromatography on silica gel using a cyclohexane/ethyl acetate (80:20 by volume) mixture as eluant. The residue obtained (1.2 g) is recrystallized in an acetone/water (1:3 by volume) mixture. 4-Phenyl-2-quinolyl N,N-diethylcarbamate (0.83 g), m.p. 64° C., is thereby obtained.

EXAMPLE 37

Triethylamine (38 cc) and diethylcarbamoyl chloride (34.5 cc) are added in 4 portions and at 24-hour intervals to 4-phenyl-2-quinazolinol (10 g) in dimethylformamide (100 cc) at 60° C. After the mixture is cooled, water (300 cc) is added and the aqueous phase extracted with methylene chloride (3×200 cc). After evaporation of the solvent, the residual solid is taken up in ethyl ether (100 cc), and the mixture is filtered and evaporated again. The residue is dissolved in hot ethyl acetate (100 cc), the solution is filtered and the solvent evaporated off.

The crude product (4 g) obtained is recrystallized in isopropanol. 4-Phenyl-2-quinazolinyl diethylcarbamate (2.5 g), m.p. 112° C., is recovered.

4-Phenyl-2-quinazolinol can be prepared according to GABRIEL, Ber., 29, 1310 (1896).

EXAMPLE 38

The procedure is as in Example 37, starting with 2-phenyl-4-quinazolinol (10 g), triethylamine (50 cc) and diethylcarbamoyl chloride (45.5 cc) in dimethylformamide (100 cc).

The purification of crude product is performed by several chromatographic separations on silica gel, first with a cyclohexane/ethyl acetate (7:3 by volume) mixture as eluant, then chloroform/methanol (95:5 by volume) and finally cyclohexane/diethylamine (95:5 by volume). A final recrystallization in petroleum ether yields 2-phenyl-4-quinazolinyl diethylcarbamate (1.2 g), m.p. 54° C.

2-phenyl-4-quinazolinol can be prepared according to H. STEPHEN, J. Chem. Soc., 4420 (1956).

EXAMPLE 39

The procedure is as in Example 37, starting with 1-phenyl-3-isoquinolinol (3.5 g), triethylamine (7.2 g) and diethylcarbamoyl chloride (9.63 g) in dimethylformamide (35 cc). The product is purified by chromatography on silica gel with a cyclohexane/ethyl acetate (4:1 by volume) mixture as eluant. On crystallization using isopropyl ether, 1-phenyl-3-isoquinolyl diethylcarbamate (0.8 g), m.p. 76° C., is obtained.

1-Phenyl-3-isoquinolinol can be prepared according to D. W. JONES, J. Chem. Soc., 1729 (1969).

EXAMPLE 40

The procedure is as in Example 37, starting with 3-phenyl-1-isoquinolinol (4.1 g), triethylamine (7.5 g) and diethylcarbamoyl chloride (10 g) in dimethylformamide (40 cc).

After chromatography on silica gel with a cyclohexane/ethyl acetate (4:1 by volume) mixture as eluant and crystallization in isopropyl ether, 3-phenyl-1-isoquinolyl diethylcarbamate (2.7 g), m.p. 81° C., is obtained.

3-Phenyl-1-isoquinolinol can be prepared according to GABRIEL, Chem. Ber., 18, 3471 (1885).

EXAMPLE 41

The procedure is as in Example 37, starting with 3-(4-methylphenyl)-1-isoquinolinol (4.7 g), triethylamine (8.1 g) and diethylcarbamoyl chloride (10.8 g) in dimethylformamide (50 cc). After chromatography on silica gel with a cyclohexane/ethyl acetate (4:1 by volume) mixture as eluant and recrystallization in ethyl ether, 3-(4-methylphenyl)-1-isoquinolyl diethylcarbamate (0.6 g), m.p. 98° C., is obtained.

3-(4-Methylphenyl)-1-isoquinolinol can be prepared according to A KASAHARA et al., Chem. Ind. (LONDON), (16), 666, (1980).

EXAMPLE 42

The procedure is as in Example 37, starting with 3-(4-methoxyphenyl)-1-isoquinolinol (10 g), triethylamine (16 g) and diethylcarbamoyl chloride (21.7 g) in dimethylformamide (100 cc). After chromatography on silica gel, initially with a cyclohexane/ethyl acetate (1:1 by volume) mixture and the second time with a toluene/methanol (98:2 by volume) mixture as eluants, and crystallization in 80% strength aqueous ethanol, 3-(4-methoxyphenyl)-1-isoquinolyl diethylcarbamate (0.7 g), m.p. 84° C., is obtained.

3-(4-Methoxyphenyl)-1-isoquinolinol can be prepared according to W. T. BOYCE et al., J. Org. Chem., 31, 3807 (1966).

EXAMPLE 43

2-[(2-Phenyl-4-quinolyl)oxy]propionic acid (2.93 g) and thionyl chloride (2.2 cc) in chloroform (75 cc) are heated under reflux for 8 hours 30 minutes. The solvents are removed under reduced pressure and the residue obtained is added, in the course of 15 minutes, to a solution, cooled beforehand to 5° C., of diethylamine (10.3 cc) in methylene chloride (100 cc). The mixture is stirred for 1 hour 30 minutes at 5°-10° C. and the organic phase washed with water (6×100 cc), dried over magnesium sulphate and evaporated under reduced pressure. The residue obtained is chromatographed on silica gel using a cyclohexane/ethyl acetate (50:50 by volume) mixture as eluant.

The residue obtained is recrystallized in isopropyl ether. N,N-Diethyl-2-[(2-phenyl-4-quinolyl)oxy]-propanamide (2.09 g), m.p. 130° C., is thereby isolated.

2-[(2-Phenyl-4-quinolyl)oxy]propionic acid can be prepared by saponification of the corresponding ethyl ester using normal sodium hydroxide solution. Its m.p. is 124° C.

Ethyl 2-[(2-phenyl-4-quinolyl)oxy]propionate can be prepared in the following manner:

Ethyl 2-bromopropionate (4.3 cc) is added dropwise to a stirred suspension of 2-phenyl-4-quinolinol (6.63 g) and potassium carbonate (8.3 g) in methyl ethyl ketone (200 cc). The mixture is heated for three hours under reflux. The mixture is brought back to room temperature (approximately 20° C.), the insoluble material drained and the solvents removed under reduced pressure. The residue is taken up with 40°-70° petroleum ether (100 cc) and drained. Ethyl 2-[(2-phenyl-4-quinolyl)oxy]propionate (9.2 g), m.p. 80° C., is thereby isolated.

EXAMPLE 44

4-[(2-Phenyl-4-quinolyl)oxy]butanoic acid (1.1 g) and thionyl chloride (0.53 cc) in chloroform (20 cc) are heated for 3 hours under reflux. The solvents are removed under reduced pressure. Chloroform (20 cc) is then added to the residue, and diethylamine (2.2 cc) is introduced dropwise with stirring. The mixture is stirred for 2 hours at room temperature (approximately 20° C.), the solvent evaporated under reduced pressure and the residue taken up with water (50 cc) and ethyl acetate (50 cc). The aqueous phase is extracted with ethyl acetate (3×20 cc) and the organic phases are combined, washed with water (50 cc), dried over magnesium sulphate and evaporated under reduced pressure. The residue obtained is chromatographed on silica gel using a cyclohexane/ethyl acetate (50:50 by volume) mixture as eluant. The residue obtained is taken up in acetone and, after addition of a solution of hydrochloric acid in ethyl ether, N,N-diethyl-4-[(2-phenyl-4-quinolyl)oxy]butanamide hydrochloride (0.47 g), m.p. 140° C., is isolated.

4-[(2-Phenyl-4-quinolyl)oxy]butanoic acid can be prepared in the following manner:

1 —Preparation of 4-[(2-phenyl-4-quinolyl)oxy]-butanol.

Sodium (0.713 g) is added in small pieces with stirring to methanol (30 cc). The mixture is stirred for 10 minutes at room temperature (approximately 20° C.) and 1,4-butanediol (24.8 cc) is then added. The mixture is then heated so as to remove the methanol by distillation up to 160° C., and this temperature is maintained for 15 minutes. The mixture is cooled to 100° C. and, under an atmosphere of nitrogen, copper powder (30 mg) is added with stirring and 4-bromo-2-phenylquinoline (7 g) is then added in small portions in the course of 30 minutes. The mixture is then heated to 160° C. for 2 hours. After being cooled to room temperature (approximately 20° C.), the reaction medium is taken up with water, the copper removed by filtration and the filtrate extracted with chloroform. The organic phase is washed with water, dried over magnesium sulphate and evaporated under reduced pressure. After two recrystallizations in a cyclohexane/ethyl acetate (70:30 by volume) mixture, 4-[(2-phenyl-4-quinolyl)oxy]butanol (2.83 g), m.p. 112° C., is isolated. 4-Bromo-2-phenylquinoline can be prepared according to KASLOW et al., J. Amer. Chem. Soc., 72, 1723 (1950).

2—Preparation of 4-[(2-phenyl-4-quinolyl)oxy]-butanoic acid.

A solution of 4-[(2-phenyl-4-quinolyl)oxy]butanol (2.20 g) in glacial aceic acid (10 cc) is added slowly to a solution, cooled to 5° C., of chromic anhydride (2.25 g) in 90% strength acetic acid (5 cc). The temperature is allowed to rise to approximately 20° C., and the mixture is then stirred for one hour at this temperature. Ethanol (50 cc) is then added, the solvents are evaporated off under reduced pressure, the residue is taken up with water (100 cc) and the insoluble material is drained and washed several times with water. This insoluble material is taken up with normal sodium hydroxide solution (15 cc) and heated under reflux for two hours. The insoluble material is removed by filtration and the filtrate acidified by adding glacial acetic acid. The precipitate obtained is drained. 4-[(2-Phenyl-4-quinolyl)oxy]-butanoic acid (0.740 g), m.p. 264° C., is obtained.

EXAMPLE 45

The procedure is as in Example 44, but starting with 3-[(2-phenyl-4-quinolyl)oxy]propanoic acid (1.25 g), thionyl chloride (1.25 cc) in chloroform (100 cc) and diethylamine (2.66 cc). After chromatography of the residue on silica gel using the eluant cyclohexane/ethyl acetate (50:50 by volume), N,N-diethyl-3-[(2-phenyl-4-quinolyl)oxy]propanamide (0.43 g), m.p. 94° C., is isolated.

3-[(2-Phenyl-4-quinolyl)oxy]propanoic acid, which has an m.p. of 172° C., can be prepared by oxidation of [(2-phenyl-4-quinolyl)oxy]propanol, which is itself prepared by reacting 4-bromo-2-phenylquinoline on the monosodium salt of 1,3-propanediol, following the processes described in Example 44 for the preparation of 4-[(2-phenyl-4-quinolyl)oxy]butanoic acid.

EXAMPLE 46

N,N-Diethyl-2-chloroacetamide (3.3 g) is added to a stirred suspension of 4-phenyl-2-quinolinol (4.42 g), potassium carbonate (5.52 g) and cuprous iodide (0.95 g) in 2-butanone (200 cc). The mixture is heated under reflux for 21 hours. The mixture is brought back to room temperature (approximately 20° C.), the insoluble material filtered on a sintered filter and the filtrate evaporated to dryness under reduced pressure.

The residue obtained is chromatographed on silica gel using a cyclohexane/ethyl acetate (50:50 by volume) mixture as eluant. N,N-Diethyl-(4-phenyl-2-quinolyl)oxy acetamide (3.9 g), which has an m.p. of 100° C. after recrystallization in isopropyl ether is thereby isolated.

EXAMPLE 47

A mixture of 2-phenyl-4-quinazolinol (4.45 g), N,Ndiethylchloroacetamide (3.3 g), sodium carbonate (4.25 g) and cuprous iodide (1 g) in 2-butanone (70 cc) is brought to boiling for 22 hours. The solvent is evaporated off under reduced pressure, water (100 cc) is added, the mixture is alkalinised with ammonia solution and the aqueous phase is extracted with methylene chloride (3×100 cc). The organic phase is dried over magnesium sulphate and evaporated to dryness under reduced pressure. The residue is chromatographed on silica gel with a cyclohexane/ethyl acetate (1:1 by volume) mixture as eluant. After crystallization in isopropyl ether, N,N-diethyl-(2-phenyl-4-quinazolinyl)oxyacetamide (4 g), m.p. 113° C., is obtained.

EXAMPLE 48

The procedure is as in Example 47, starting with 4-phenyl-2-quinazolinol (4.45 g), N,N-diethylchloroacetamide (6.6 g), sodium carbonate (4.25 g) and cuprous iodide (1 g) in 2-butanone (70 cc).

After chromatography on silica gel with ethyl acetate as eluant and recrystallization in isopropyl ether, N,N-diethyl-(4-phenyl-2-quinazolinyl)oxyacetamide (1 g) m.p. 88° C., is obtained.

EXAMPLE 49

The procedure is as in Example 47, starting with 3-phenyl-1-isoquinolinol (5.1 g), N,N-diethylchloroacetamide (3.8 g), sodium carbonate (4.8 g) and cuprous iodide (1.15 g) in 2-butanone (100 cc). After 2 chromatographic separations on silica gel with chloroform as eluant and crystallization of the product in petroleum ether, N,N-diethyl-(3-phenyl-1-isoquinolyl)oxyacetamide (0.5 g), m.p. 102° C., is obtained.

EXAMPLE 50

The procedure is as in Example 47, starting with 1-phenyl-3-isoquinolinol (4.4 g), N,N-diethyl-2-chloroacetamide (3.3 g), sodium carbonate (4.25 g) and cuprous iodide (1 g) in 2-butanone (90 cc). After chromatography on silica gel with a chloroform/methanol (98:2 by volume) mixture as eluant and crystallization of the product in isopropyl ether, N,N-diethyl-(1-phenyl-3-isoquinolyl)oxyacetamide (2.6 g), m.p. 105° C., is obtained.

EXAMPLE 51

The procedure is as in Example 7, starting with 2-[(3-phenyl-1-isoquinolyl)oxy]propanoic acid (0.78 g), carbonyldiimidazole (0.52 g) and diethylamine (0.82 cc) in anhydrous tetrahydrofuran (20 cc).

After chromatography on silica gel with a cyclohexane/ethyl acetate (1:1 by volume) mixture as eluant and recrystallization in isopropyl ether, N,N-diethyl-2-[(3-phenyl-1-isoquinolyl)oxy]propanamide (0.53 g), m.p. 117° C., is obtained.

2-[(3-Phenyl-1-isoquinolyl)oxy]propanoic acid is prepared according to the following process:

A mixture of 3-phenyl-1-isoquinolinol (2.42 g), ethyl α-bromopropionate (8 cc) and sodium carbonate (5.4 g) in 2-butanone (20 cc) is brought to boiling for 96 hours.

The solvent is evaporated off under reduced pressure. Water (50 cc) is added and the aqueous phase extracted with chloroform (3×50 cc). The organic phase is dried over magnesium sulphate and the solvent evaporated off under reduced pressure. The residue is chromatographed on silica gel with a cyclohexane/ethyl acetate (1:1 by volume) mixture as eluant. After evaporation, the first fractions yield a product (1 g) which is treated for 1 hour with sodium hydroxide solution (2 cc) and ethanol (20 cc) at room temperature (approximately 20° C.). The ethanol is removed under reduced pressure, water (50 cc) is added and the aqueous phase is washed with ethyl ether (50 cc), the aqueous phase is acidified with concentrated hydrochloric acid and extracted with chloroform (3×50 cc). The organic phase is dried over magnesium sulphate, filtered and evaporated to dryness under reduced pressure. 2-[(3-Phenyl-1-isoquinolyl)oxy]propanoic acid (0.78 g) is obtained.

EXAMPLE 52

A mixture of 2-phenyl-4-quinazolinol (4.45 g), N,N-diethyl-2-bromopropanamide (4.2 g) and sodium carbonate (4.24 g) in 2-butanone (50 cc) is brought to boiling for 9 hours. After being cooled, the mixture is filtered and the filtrate evaporated to dryness under reduced pressure. The residue is extracted with a cyclohexane/ethyl acetate (7:3 by volume) mixture (50 cc) at 60° C., the insoluble material is filtered off and the filtrate evaporated to dryness under reduced pressure. The residual solid is chromatographed on silica gel with a cyclohexane/ethyl acetate (7:3 by volume) mixture as eluant. After 3 recrystallizations in an ethanol/water (2:1 by volume) mixture, N,N-diethyl-2-[(2-phenyl-4-quinazolinyl)oxy]propanamide (0.96 g), m.p. 160° C., is obtained.

EXAMPLE 53

The separation of the 2 enantiomers is carried out starting with N,N-diethyl-2-[(2-phenyl-4-quinazolinyl)oxy]propanamide (1 g) obtained according to Example 52.

HPLC chromatography is performed on a covalent DNBPG (dinitrobenzoylphenylglycine) chiral column of J. T. BAKER, using a hexane/isopropyl alcohol (95:5 by volume) mixture as eluant. The flow rate is 0.7 cc/min and the number of injections was one hundred.

After evaporation of the best fractions and crystallization in 80% strength aqueous ethanol, dextrorotatory N,N-diethyl-2-[(2-phenyl-4-quinazolinyl)oxy]propanamide (200 mg), m.p. 160° C., $[\alpha]_D^{24} = +48.7°$ (0.5% in N HCl) and laevorotatory N,N-diethyl-2-[(2-phenyl-4-quinazolinyl)oxy]propanamide (200 mg), m.p. 160° C., $[\alpha]_D^{24} = -52.0°$ (0.5% in N HCl), are recovered.

EXAMPLE 54

Thionyl chloride (0.65 cc) is added to a supension of [(2-phenyl-4-quinolyl)thio]acetic acid (2.4 g) in chloroform (24 cc), and the mixture is stirred for two hours at room temperature (approximately 20° C.). The reaction mixture is cooled to 5° C. and diethylamine (2.5 cc) is then added with stirring. The mixture is then stirred for one hour at room temperature (approximately 20° C.), the solvents are evaporated off under reduced pressure and the residue is taken up with water (50 cc) and ethyl acetate (50 cc); the organic phase is decanted and the aqueous phase extracted with ethyl acetate (50 cc). The organic phases are combined, washed with water (2×20 cc), then with normal ammonium hydroxide solution (20 cc) and finally with water (2×10 cc), dried over magnesium sulphate and evaporated under reduced pressure. The residue obtained is chromatographed on silica gel with a cyclohexane/ethyl acetate (50:50 by volume) mixture. The oil obtained (1 g) is taken up in acetone and, after addition of a solution of hydrochloric acid in ethyl ether and recrystallization of the crude hydrochloride in ethanol, N,N-diethyl-[(2-phenyl-4-quinolyl)thio]acetamide hydrochloride (0.68 g), m.p. 150° C., is obtained.

[(2-Phenyl-4-quinolyl)thio]acetic acid is prepared in the following manner:

4-Chloro-2-phenylquinoline (3 g) and thioglycolic acid (1.38 g) in pyridine (40 cc) are heated under reflux for 4 hours. After evaporation of the pyridine under reduced pressure, the residue is taken up with water (125 cc) and normal aqueous sodium hydroxide solution (40 cc). The aqueous phase is washed with ethyl ether (2×50 cc), acidified to pH 5 with glacial acetic acid and extracted with ethyl ether (3×50 cc). The ether phase is washed with water, dried over magnesium sulphate and evaporated under reduced pressure. [(2-Phenyl-4-quinolyl)thio]acetic acid (3.2 g), m.p. 138° C., is thereby obtained.

4-Chloro-2-phenylquinoline can be prepared according to BANGDIWALA et al., J. Indian Chem. Soc. 31, 43 (1954).

EXAMPLE 55

Thionyl chloride (1.24 cc) is added to a suspension of 2-[2-phenyl-4-quinolyl)thio]propionic acid (4.8 g) in chloroform (48 cc). The mixture is stirred for 15 minutes at room temperature (approximately 20° C.) and then heated under reflux for 2 hours 30 minutes. The temperature is brought back to 5° C. and diethylamine (4.9 cc) is then introduced in the course of 20 minutes. The mixture is stirred for 30 minutes at 50° C. and then 30 minutes at room temperature (approximately 20° C.). The solvents are evaporated off under reduced pressure and the residue is taken up with water (50 cc) and ethyl ether (80 cc). The organic phase is decanted and the aqueous phase extracted with ethyl ether (2×50 cc). The organic phases are combined, washed with water (2×20 cc), 0.1N sodium hydroxide solution (20 cc, once) and water (2×10 cc), dried over sodium sulphate and evaporated under reduced pressure. The residue obtained is taken up in ethanol and, after addition of a solution of hydrochloric acid in ethyl ether and 2 recrystallizations in ethanol, N,N-diethyl-2-[(2-phenyl-4-quinolyl)thio]propanamide hydrochloride (1.95 g), m.p. 155° C., is isolated.

2-[(2-Phenyl-4-quinolyl)thio]propionic acid can be prepared in a similar manner to 2-[(2-phenyl-4-quinolyl)thio]acetic acid described in Example 54, starting with 4-chloro-2-phenylquinoline (4.8 g), thiolactic acid (2.54 g) and pyridine (50 cc) on a sieve. 2-[(2-Phenyl-4-quinolyl)thio]propionic acid (5.3 g) is thereby obtained, the proton NMR spectrum of which, in deuterated chloroform, has the following characteristics:

| S—C$\underline{H}$(CH$_3$)—COOH | δ: 4.70 ppm | H$_3$ | δ: 8.14 ppm |
|---|---|---|---|
| S—CH(C$\underline{H}_3$)—COOH | δ: 1.65 ppm | H$_{5,8}$ | δ: 8.22 ppm |

EXAMPLE 56

The procedure is as in Example 54, but starting with 3-[(2-phenyl-4-quinolyl)thio]propionic acid (3.4 g), thionyl chloride (0.88 cc) and diethylamine (3.5 cc).

The residue obtained is taken up in ethanol and, after addition of a solution of hydrochloric acid in ethyl ether and recrystallization in ethanol, N,N-diethyl-3-[(2-phenyl-4-quinolyl)thio]propanamide hydrochloride (2.3 g), m.p. 145° C., is isolated.

3-[(2-Phenyl-4-quinolyl)thio]propionic acid is prepared in the following manner:

4-Chloro-2-phenylquinoline (4.8 g) and 3-mercaptopropionic acid (2.54 g) in pyridine (50 cc) are heated under reflux for 11 hours. After a treatment similar to that described in Example 54 for 2-[(2-phenyl-4-quinolyl)thio]acetic acid, 3-[(2-phenyl-4-quinolyl)thio]propionic acid (3.4 g) is isolated, the proton NMR spectrum of which, in deuterated chloroform, has the following characteristics:

| S—C$\underline{H}_2$ | δ: 3.42 ppm | H$_3$ | δ: 7.62 ppm |
|---|---|---|---|
| —C$\underline{H}_2$—COOH | δ: 2.80 ppm | H$_{5,8}$ | δ: 8 ppm |

EXAMPLE 57

Potassium carbonate (4.65 g) and then 4-phenyl-2-quinolinethiol (4 g) are added to a solution of N,N-diethyl-2-bromoacetamide (3.3 g) in methyl ethyl ketone (120 cc). The mixture is stirred for 10 minutes at room temperature (approximately 20° C.) and then heated under reflux for 15 minutes. The inorganic salts are removed by filtration and washed with methyl ethyl ketone (3×10 cc). The filtrates are combined and evaporated under reduced pressure; the residue is taken up with ethyl ether (200 cc), and the organic phase washed with water (2×50 cc), dried over magnesium sulphate and evaporated under reduced pressure.

The residue obtained is taken up in acetone and, after addition of a solution of hydrochloric acid in ethyl ether and recrystallization in ethanol, N,N-diethyl-[(4-phenyl-2-quinolyl)thio]acetamide hydrochloride (2.6 g) is obtained.

4-Phenyl-2-quinolinethiol can be prepared by heating 2-chloro-4-phenylquinoline with sodium hydrogen sulphide at 170° C. in a glycol/Dowtherm mixture.

EXAMPLE 58

A solution of sodium periodate (5.5 g) in water (38 cc) warmed beforehand to 50° C., is added in the course of 10 minutes to a solution of N,N-diethyl-3-[(2-phenyl-4-quinolyl)thio]propanamide (4.7 g), prepared according to Example 56, in ethanol (76 cc). This mixture is stirred for 3 days at room temperature (approximately 20° C.). The ethanol is evaporated off under reduced pressure and the residue taken up with water (100 cc) and ethyl acetate (200 cc). The organic phase is decanted, washed with water (2×50 cc), dried over magnesium sulphate and evaporated under reduced pressure.

The residue is chromatographed on silica gel using a chloroform/ethyl acetate (70:30 by volume) mixture.

After recrystallization of the residue obtained in ethyl acetate, N,N-diethyl-3-[(2-phenyl-4-quinolyl)sulphinyl]propanamide (2.8 g), m.p. 130° C., is obtained.

EXAMPLE 59

Methanesulphonic acid (0.31 cc) and 30% strength hydrogen peroxide solution (0.53 cc) are added to a solution of N,N-diethyl-3-[(2-phenyl-4-quinolyl)sulphinyl]propanamide (1.8 g), prepared according to Example 58, in glacial acetic acid (18 cc). The mixture is heated to 80° C. for 3 hours with stirring. The mixture is cooled to room temperature (approximately 20° C.), concentrated ammonium hydroxide solution (1 cc) is added, followed by water (180 cc), and the mixture is extracted with ethyl ether (3×100 cc). The ether phase is washed with 0.1N ammonium hydroxide solution (50 cc) and then with water (50 cc), and dried over magnesium sulphate. After any peroxides present have been destroyed by adding sodium sulphite, and the solvents concentrated under reduced pressure, the residue (1.8 g) obtained is chromatographed on silica gel using a cyclohexane/ethyl acetate (50:50 by volume) mixture as eluant. After recrystallization of the residue in ethyl acetate, N,N-diethyl-3-[(2-phenyl-4-quinolyl)sulphonyl]-propanamide (0.82 g), m.p. 100° C., is obtained.

EXAMPLE 60

4-Bromo-2-phenylquinoline (3 g), phenol (1.97 g) and N,N-diethyl-2-ethylaminoacetamide (1.66 g) are heated to 140° C. for 3 hours, N,N-diethyl-2-ethylaminoacetamide (1.66 g) is then added again and the mixture is then heated to 140° C. for a further 2 hours. The reaction medium is taken up with a water/ethyl ether mixture, and then acidified by adding decinormal hydrochloric acid solution; the acidic aqueous phase is washed with ethyl ether, alkalinised to pH 10 by adding concentrated ammonium hydroxide solution and extracted with ethyl ether (3×100 cc). The organic phase is dried over magnesium sulphate and evaporated under reduced pressure. The residue (2.5 g) thereby obtained is chromatographed on silica gel using a cyclohexane/ethyl acetate (50:50 by volume) mixture as eluant. The residue is taken up in acetone and, after addition of a solution of hydrochloric acid in ethyl ether, N,N-diethyl[ethyl-(2-phenyl-4-quinolyl)amino]acetamide hydrochloride (2.45 g), m.p. 150° C., is obtained.

N,N-Diethyl-2-ethylaminoacetamide can be prepared according to A.G. GEIGY, German Patent Application Nos. 2,411,662 and 2,447,587 (1944).

EXAMPLE 61

The procedure is as in Example 60, but starting with 4-bromo-2-phenylquinoline (7.7 g), N,N-diethyl-3-ethylaminopropanamide (4.7 g) and phenol (5 g). After an initial chromatographic separation of the residue on silica gel using a cyclohexane/ethyl acetate (50:50 by volume) mixture followed by a second chromatographic separation with a cyclohexane/ethyl acetate (70:30 by volume) mixture, the residue (1.4 g) isolated is converted to the dihydrochloride in acetone by adding a solution of hydrochloric acid in ethyl ether. After recrystallization in an acetone/ethyl ether mixture, N,N-diethyl-3-[ethyl-(2-phenyl-4-quinolyl)amino]-propanamide dihydrochloride (0.79 g), m.p. 154° C., is obtained.

N,N-Diethyl-3-ethylaminopropanamide can be prepared by methods similar to those known in the literature, MARINI, BETTOLO, CAVALLA, Gazetta Chim. Ital., 84, 896,906 (1954).

EXAMPLE 62

N,N-Diethylbromoacetamide (4.65 g) is added to a stirred suspension of 3-phenyl-1-naphthol (5.2 g) and potassium carbonate (6.6 g) in 2-butanone (150 cc).

The mixture is heated under reflux for 2 hours and cooled to room temperature (approximately 20° C.), the insoluble material is removed by filtration and the solvent evaporated under reduced pressure.

After chromatography of the residue on silica gel, using methylene chloride and then a methylene chloride/ethyl acetate (98:2 by volume) mixture as successive eluants, and crystallization of the residue obtained in isopropyl ether, N,N-diethyl-(3-phenyl-1-naphthyl)oxyacetamide (2 g), m.p. 82° C., is isolated.

3-Phenyl-1-naphthol can be prepared according to C. KIPPING et al., J. Prakt. Chem., 315 (5), 887–94 (1973).

EXAMPLE 63

3-Phenyl-1-naphthol (3.15 g), N,N-diethylcarbamoyl chloride (1.95 g), triethylamine (1.45 g) and 4-dimethylaminopyridine (0.035 g) in tetrahydrofuran (37 cc) are heated under reflux for 4 hours. N,N-diethylcarbamoyl chloride (0.4 g) is added, the mixture is heated for a further 2 hours and then cooled to room temperature (approximately 20° C.), the precipitate is removed by filtration and the filtrate is evaporated under reduced pressure. The residue obtained is chromatographed on silica gel using a cyclohexane/ethyl acetate (80:20) by volume) mixture as eluant. After recrystallization of the residue in an isopropyl ether/petroleum ether (1:1 by volume) mixture, 3-phenyl-1-naphthyl N,N-diethylcarbamate (2.94 g), m.p. 74° C., is isolated.

EXAMPLE 64

The procedure is as in Example 62, starting with 3-phenyl-1-naphthol (3 g), potassium carbonate (3.75 g) and N,N-diethyl-2-bromopropanamide (2.83 g) in 2-butanone (90 cc), adding potassium iodide (2.2 g) after 8 hours of refluxing followed by N,N-diethyl-2-bromopropanamide (0.56 g) after 10 hours of refluxing.

After recrystallization of the residue in isopropyl ether, N,N-diethyl-2-[(3-phenyl-1-naphthyl)oxy]propanamide (3.7 g), m.p. 109° C., is obtained.

EXAMPLE 65

2-[(2-Phenyl-4-quinolyl)oxy]propanoic acid (2.5 g) and thionyl chloride (1.85 cc) in chloroform (50 cc) are heated under reflux for 3 hours. The solvent is removed under reduced pressure and the residue obtained is suspended in chloroform (40 cc). Diallylamine (1.05 cc) and triethylamine (2.63 cc) in chloroform (75 cc) are added slowly to this suspension with stirring, the temperature being maintained at 10° C. The mixture is stirred for 15 minutes at room temperature (approximately 20° C.), the solvent evaporated under reduced pressure and the residue taken up with ethyl acetate (50 cc) and water (20 cc). The organic phase is decanted, washed with water (2×10 cc) and then with normal hydrochloric acid solution (10 cc) and finally with water (10 cc).

After evaporation of the solvent under reduced pressure, the residue is dissolved in acetonitrile and crystallized by slow addition of isopropyl ether. After recrystallization of the residue obtained in isopropyl ether in the presence of Acticarbone charcoal, N,N-dipropen- 2-yl-2-[(2-phenyl-4-quinolyl)oxy]propanamide (1.9 g) m.p. 110° C., is obtained.

EXAMPLE 66

The procedure is as in Example 20, starting with α-methyl-2-phenyl-4-quinolinepropanoic acid (1.8 g) in chloroform (20 cc), thionyl chloride (0.58 cc), N-methylcyclohexylamine (0.81 cc) and triethylamine (1.88 cc) in chloroform (20 cc).

The residue obtained is recrystallized in ethyl acetate. N-Cyclohexyl-N-methyl-α-methyl-2-phenyl-4-quinolinepropanamide (1.45 g), m.p. 160° C., is thereby isolated.

EXAMPLE 67

The procedure is as in Example 20, starting with α-methyl-2-phenyl-4-quinolinepropanoic acid (1.8 g) in chloroform (20 cc), thionyl chloride (0.58 cc), dihexylamine (1.44 cc) and triethylamine (1.88 cc) in chloroform (20 cc).

The residue obtained is chromatographed on silica gel using a cyclohexane/ethyl acetate (80:20 by volume) mixture as eluant. The residue is taken up in acetone and, after addition of a solution of hydrochloric acid in ethyl ether and recrystallization of the crude hydrochloride obtained in an ethanol/ethyl ether (1:3 by volume) mixture, N,N-dihexyl-α-methyl-2-phenyl-4-quinolinepropanamide hydrochloride (0.36 g), m.p. 102° C., is isolated.

EXAMPLE 68

The procedure is as in Example 20, starting with α-methyl-3-phenyl-1-naphthalenepropanoic acid (1.1 g), thionyl chloride (0.37 cc) in chloroform (20 cc) and diethylamine (2 cc) in chloroform (20 cc).

The residue is chromatographed on silica gel using a cyclohexane/ethyl acetate (70:30 by volume) mixture as eluant. N,N-Diethyl- α-methyl-3-phenyl-1-naphthalenepropanamide (1 g), m.p. 70° C., is thereby isolated.

α-Methyl-3-phenyl-1-naphthalenepropanoic acid can be prepared in the following manner:

1—Preparation of 3-phenyl-1-naphthalenemethanol.

Sodium borohydride (1.9 g) is added to a stirred solution of ethyl 3-phenyl-1-naphthalenecarboxylate (5.6 g) in tert.-butanol (80 cc). The mixture is brought to reflux and methanol (16 cc) is then run in, taking 2 hours 10 minutes. Heating is continued under reflux for a further 2 hours, the mixture is then cooled to room temperature (approximately 20° C.), water (40 cc) and then acetic acid (4 cc) are added and the mixture is evaporated under reduced pressure. The residue is taken up with chloroform (100 cc) and water (100 cc). The organic phase is decanted, washed with water (100 cc) and evaporated under reduced pressure. The residue is chromatographed on silica gel using chloroform as eluant. The fractions containing 3-phenyl-1-naphthalenemethanol are combined. After evaporation under reduced pressure, a residue obtained which is taken up with methylene chloride and washed with ammonium hydroxide solution. The organic phase is dried over magnesium sulphate and evaporated under reduced pressure.

3-Phenyl-1-naphthalenemethanol (3.6 g) is isolated, the proton NMR spectrum of which, in deuterated chloroform, has the following characteristics:

| Ar—CH₂OH | δ: 5.20 ppm |
|---|---|
| naphthalene protons | |
| H₂ | δ: 7.48 ppm |
| H₄ | δ: 7.67 ppm |
| benzene ring protons | |
| Hoo' | δ: 7.71 ppm |
| Hmm'p | δ: 7.45 ppm |

Ethyl 3-phenyl-1-naphthalenecarboxylate can be prepared by esterification of 3-phenyl-1-naphthalenecarboxylic acid by means of ethanol in the presence of sulphuric acid.

3-Phenyl-1-naphthalenecarboxylic acid can be prepared according to F. G. BADDAR et al., J. Chem. Soc., 1009 (1959).

2—Preparation of 1-chloromethyl-3-phenylnaphthalene.

Thionyl chloride (0.78 cc) is added in the course of 10 minutes to a stirred solution, cooled beforehand to 0° C., of 3-phenyl-1-naphthalenemethanol (1 g) in chloroform (20 cc), and the temperature is then allowed to rise to room temperature (approximately 20° C.). The mixture is stirred for 15 hours at this temperature and the solvent evaporated under reduced pressure. 1-Chloromethyl-3-phenylnaphthalene (1.1 g) is obtained, the proton NMR spectrum of which, in deuterated chloroform, shows the following characteristics:

| Ar—CH₂Cl | δ: 5.08 ppm |
|---|---|
| naphthalene protons | |
| H₂ | δ: 7.65 ppm |
| H₄ | δ: 7.78 ppm |
| phenyl protons Hmm'p | δ: 7.44 ppm |

3—Preparation of α-methyl-3-phenyl-1-naphthalenepropanoic acid.

Sodium hydride (0.62 g) in 60% strength dispersion in oil is added slowly to dry tetrahydrofuran (15 cc) under an atmosphere of nitrogen. A solution of diethyl methylmalonate (2.69 g) in tetrahydrofuran (15 cc) is then introduced dropwise, followed, in the course of 50 minutes, by a solution of 1-chloromethyl-3-phenylnaphthalene (1.95 g) in tetrahydrofuran (30 cc). The mixture is stirred for one hour at room temperature (approximately 20° C.) and then for 3 hours at the refluxing temperature of tetrahydrofuran. The mixture is brought back to room temperature (approximately 20° C.), and glacial acetic acid (2 cc) is added dropwise. The tetrahydrofuran is evaporated off under reduced pressure, and the residue taken up with water (100 cc) and extracted with ethyl ether (2×50 cc). The ether phase is washed with water, dried over magnesium sulphate and evaporated under reduced pressure. The residue obtained is taken up with concentrated hydrochloric acid solution (25 cc) and glacial acetic acid (25 cc). The mixture is heated under reflux for 4 hours, the acids are evaporated off as completely as possible under reduced pressure and the residue is taken up with water (100 cc), alkalinised to pH 10 by adding concentrated ammonium hydroxide solution and extracted with ethyl ether (2×50 cc).

The aqueous phase is acidified to pH 6 by adding acetic acid and extracted with ethyl acetate (2×50 cc). The organic phase is dried over magnesium sulphate and evaporated under reduced pressure. The residue obtained is chromatographed on silica gel using a chloroform/acetic acid (9:1 by volume) mixture as eluant. α-Methyl-3-phenyl-1-naphthalenepropanoic acid (1 g) is isolated, the proton NMR spectrum of which, in deuterated chloroform, shows the following characteristics:

| Aromatic protons | δ: 7.3 to 8.2 ppm |
|---|---|
| Ar—CH$_2$, Ar—CH$_2$—CH— | δ: 2.7 to 3.5 ppm |
| Ar—CH(CH$_3$)— | δ: 1.2 ppm |

EXAMPLE 69

4-Phenyl-2-quinolinethiol (3 g), N,N-diethylcarbamoyl chloride (3.43 g), triethylamine (2.55 g) and 4-dimethylaminopyridine (0.68 g) in tetrahydrofuran (30 cc) are heated under reflux for 1 hour 45 minutes. The mixture is cooled to room temperature, the tetrahydrofuran evaporated off under reduced pressure and the residue taken up with water (20 cc) and ether (50 cc). The organic phase is decanted and the aqueous phase washed with ether (3×50 cc). The organic phases are combined, washed with water, dried over magnesium sulphate and evaporated under reduced pressure. The residue obtained is taken up in acetone and, after addition of a solution of hydrochloric acid in ether and recrystallization in an acetone/ether mixture, S-4-phenyl-2-quinolyl diethylcarbamothioate hydrochloride (1.05 g), m.p. 84° C., is isolated.

4-Phenyl-2-quinolinethiol can be prepared according to KUENZLE, F. M. et al., Helv. Chim. Acta 1970, 53 (4) 798-804.

EXAMPLE 70

2-Phenyl-4-quinolinethiol (4 g , N,N-diethylcarbamoyl chloride (4.57 g), triethylamine (3.4 g) and 4-dimethylaminopyridine (0.9 g) in tetrahydrofuran (40 cc) are heated under reflux for two hours 45 minutes. The mixture is cooled to room temperature, the precipitate removed by filtration and the filtrate evaporated under reduced pressure. The residue is taken up with water (20 cc) and ethyl acetate (50 cc).

The organic phase is decanted and the aqueous phase is washed with ethyl acetate (2×50 cc). The organic phases are combined, dried over magnesium sulphate and evaporated under reduced pressure. The residue is chromatographed on silica gel, initially using a toluene/diethylamine eluant and then a second time using a cyclohexane/ethyl acetate (80:20 by volume) eluant.

The residue obtained is taken up in acetone and, after addition of a solution of hydrochloric acid in ether, S-2-phenyl-4-quinolyl diethylcarbamothioate hydrochloride (3.2 g), m.p. 122° C., is isolated.

2-Phenyl-4-quinolinethiol can be prepared according to JOHN, J. Prakt Chem. (2), 119, 49.

EXAMPLE 71

The procedure is as in Example 20, starting with 2-[(2-phenyl-4-quinolyl)oxy]propanoic acid (1.2 g) in chloroform (40 cc), thionyl chloride (0.89 cc), thiomorpholine (0.41 g) and triethylamine (1.15 cc) in chloroform (20 cc).

The residue is chromatographed on silica gel using methylene chloride and then a methylene chloride/ethyl acetate (95:5 by volume) mixture as successive eluants. 4-{2-[(2-Phenyl-4-quinolyl)oxy]propionyl}thiomorpholine (0.7 g), m.p. 198° C., is obtained.

EXAMPLE 72

The procedure is as in Example 70, starting with 6-nitro-2-phenyl-4-hydroxyquinoline (6 g) in tetrahydrofuran (60 cc), N,N-diethylcarbamoyl chloride (6.1 g), triethylamine (6.3 cc) and 4-dimethylaminopyridine (1.3 g). The residue is recrystallized twice in ethyl acetate. 6-Nitro-2-phenyl-4-quinolyl diethylcarbamate (6.4 g), m.p. 140° C., is thereby obtained.

EXAMPLE 73

The procedure is as in Example 70, starting with 8-trifluoromethyl-2-phenyl-4-hydroxyquinoline (5 g) in tetrahydrofuran (50 cc), N,N-diethylcarbamoyl chloride (4.7 g), triethylamine (4.8 cc) and 4-dimethylaminopyridine (1.1 g).

After chromatography of the residue on silica gel, using a cyclohexane/ethyl acetate (80:20 by volume) mixture as eluant, and recrystallization in an isopropyl ether/petroleum ether mixture, 8-trifluoromethyl-2-phenyl-4-quinolyl diethylcarbamate (1.38 g), m.p. 79° C., is obtained.

8-Trifluoromethyl-2-phenyl-4-hydroxyquinoline can be prepared by the action of ethyl benzoyl acetate (0.12 mole) on 2-trifluoromethylaniline (0.12 mole) at 140° C. in the presence of polyphosphoric acid (86 g). Its m.p. is 136° C.

EXAMPLE 74

The procedure is as in Example 63, starting with 4-phenyl-2-naphthol (2.1 g), N,N-diethylcarbamoyl chloride (2.6 g), triethylamine (2.7 cc) and 4-dimethylaminopyridine (0.05 g) in tetrahydrofuran (20 cc).

After three successive chromatographic separations of the residue in a cyclohexane/ethyl acetate (80:20 by volume) mixture, 4-phenyl-2-naphthyl diethylcarbamate (0.5 g) is isolated, the proton NMR spectrum of which, in deuterated chloroform, has the following characteristics:

| H$_1$: | δ = 7.6 ppm |
|---|---|
| H$_3$: | δ = 7.25 ppm |
| H$_5$ and H$_8$: | δ = 7.85 ppm |
| The other aromatic protons: | δ between 7.3 and 7.6 ppm. |

4-Phenyl-2-naphthol can be prepared according to KOPTYUG and ANDREEVA, Zh. Org. Khim. 1971, 7 (II) 2398-403.

EXAMPLE 75

The procedure is as in Example 33, starting with 2-(4-methoxyphenyl)-4-quinolinol (2.7 g), triethylamine (3 cc) and N,N-diethylcarbamoyl chloride (3 g) in dimethylformamide (15 cc).

The residue is purified as in Example 33; the crude hydrochloride is recrystallized in ethyl acetate. 2-(4-Methoxyphenyl)-4-quinolyl diethylcarbamate hydrochloride (0.8 g), m.p. 107° C., is thereby isolated.

2-(4-Methoxyphenyl)-4-hydroxyquinoline can be prepared according to SORM, Chem. Listy 49, 901 (1954).

EXAMPLE 76

The procedure is as in Example 33, starting with 2-phenyl-4-quinolinol (2.6 g), triethylamine (2.5 cc) and 4-chloroformylmorpholine (2.7 g) in dimethylformamide (15 cc), and reducing the heating time to 3 hours.

The residue is chromatographed on silica gel using a cyclohexane/ethyl acetate (80:20 by volume) mixture as eluant, and then recrystallized in isopropyl ether.

2-Phenyl-4-quinolyl 4-morpholinecarboxylate (1.3 g), m.p. 127° C., is thereby isolated.

2-Phenyl-4-quinolinol can be prepared according to C. HAUSER and A. REYNOLDS, J.A.C.S. 70, 2402 (1948).

EXAMPLE 77

The procedure is as in Example 70, starting with 2-(3-trifluoromethylphenyl)-4-hydroxyquinoline (3.3 g), N,N-diethylcarbamoyl chloride (3.1 g), triethylamine (3.2 cc) and 4-dimethylaminopyridine (0.9 g) in tetrahydrofuran (33 cc).

After chromatography of the residue on silica gel using a cyclohexane/ethyl acetate (80:20 by volume) mixture as eluant, 2-(3-trifluoromethylphenyl)-4-quinolyl diethylcarbamate (1.35 g), m.p. 96° C., is isolated.

2-(3-Trifluoromethylphenyl)-4-hydroxyquinoline can be prepared by the action of ethyl 3-trifluoromethylbenzoylacetate (0.245 mole) on aniline (0.245 mole) at 160° C. in the presence of polyphosphoric acid (156 g).

EXAMPLE 78

The procedure is as in Example 70, starting with 2-(4-methylphenyl)-4-hydroxyquinoline (5 g), N,N-diethylcarbamoyl chloride (5.8 g), triethylamine (6 cc) and 4-dimethylaminopyridine (1.35 g) in tetrahydrofuran (50 cc).

The residue is chromatographed on silica gel using a cyclohexane/ethyl acetate (80:20 by volume) mixture as eluant.

The residue is taken up in ethyl ether and, after addition of a solution of hydrochloric acid in isopropanol, 2-(4-methylphenyl)-4-quinolyl diethylcarbamate hydrochloride (6.5 g), m.p. 116° C., is isolated.

2-(4-Methylphenyl)-4-hydroxyquinoline can be prepared by the action of ethyl 4-methylbenzoylacetate (0.294 mole) on aniline (0.294 mole) at 140° C. in the presence of polyphosphoric acid (168 g). Its m.p. is above 268° C.

EXAMPLE 79

The procedure is as in Example 70, starting with 2-(2-fluorophenyl)-4-hydroxyquinoline (2 g), N,N-diethylcarbamoyl chloride (2.27 g), triethylamine (2.35 cc) and 4-dimethylaminopyridine (0.55 g) in tetrahydrofuran (20 cc).

The residue is chromatographed on silica gel using a cyclohexane/ethyl acetate (70:30 by volume) mixture as eluant.

The residue is taken up in ethyl ether and, after addition of a solution of hydrochloric acid in isopropanol, 2-(2-fluorophenyl)-4-quinolyl diethylcarbamate hydrochloride (2.4 g), m.p. 123° C., is isolated.

2-(2-Fluorophenyl)-4-hydroxyquinoline can be prepared by the action of ethyl 2-fluorobenzoylacetate (0.05 mole) on aniline (0.05 mole) at 160° C. in the presence of polyphosphoric acid (25 g). Its m.p. is 224° C.

EXAMPLE 80

The procedure is as in Example 70, starting with 2-(2-thienyl)-4-hydroxyquinoline (3 g), N,N-diethylcarbamoyl chloride (3.58 g), triethylamine (3.7 cc) and 4-dimethylaminopyridine (0.5 g) in tetrahydrofuran (30 cc).

The residue is taken up in ethyl ether and, after addition of a solution of hydrochloric acid in isopropanol, a crude hydrochloride is isolated. The latter is taken up with ethyl acetate (150 cc), water (150 cc) and normal sodium hydroxide solution (40 cc). The organic phase is decanted, washed with water, dried over magnesium sulphate and evaporated under reduced pressure. The residue obtained is crystallized in petroleum ether. 2-(2-Thienyl)-4-quinolyl diethylcarbamate (2.3 g), m.p. 72° C., is thereby isolated.

2-(2-Thienyl)-4-hydroxyquinoline can be prepared by the action of ethyl 2-thenoylacetate (0.103 mole) on aniline (0.103 mole) at 160° C. in the presence of polyphosphoric acid (45.8 g). Its m.p. is above 268° C.

EXAMPLE 81

The procedure is as in Example 70, starting with 2-(4-pyridyl)-4-hydroxyquinoline (4.44 g), N,N-diethylcarbamoyl chloride (5.42 g), triethylamine (5.6 cc) and 4-dimethylaminopyridine (0.5 g) in tetrahydrofuran (45 cc).

After chromatography of the residue on silica gel using a cyclohexane/ethyl acetate (20:80 by volume) mixture, a residue is isolated and purified via a crude hydrochloride, as in Example 80.

2-(4-Pyridyl)-4-quinolyl diethylcarbamate (1.15 g), m.p. 76° C., is thereby isolated.

2-(4-Pyridyl)-4-hydroxyquinoline can be prepared by the action of ethyl isonicotinylacetate (0.08 mole) on aniline (0.08 mole) at 160° C. in the presence of polyphosphoric acid (36 g). Its m.p. is 246° C.

EXAMPLE 82

The procedure is as in Example 70, starting with 2-(3-chlorophenyl)-4-hydroxyquinoline (1.8 g), N,N-diethylcarbamoyl chloride (1.8 cc), triethylamine (2 cc) and 4-dimethylaminopyridine (0.2 g) in anhydrous tetrahydrofuran (20 cc).

After two successive chromatographic separations of the residue on silica gel, the first using a cyclohexane/ethyl acetate (50:50 by volume) mixture and the second using a cyclohexane/ethyl acetate (90:10 by volume) mixture, and crystallization in 40°-60° petroleum ether, 2-(3-chlorophenyl)-4-quinolyl diethylcarbamate (1.15 g), m.p. 83° C., is isolated.

2-(3-Chlorophenyl)-4-hydroxyquinoline can be prepared by the action of ethyl 3-chlorobenzoylacetate (0.025 mole) on aniline (0.025 mole) at 160° C. in the presence of polyphosphoric acid (11 g). Its m.p. is 210° C.

EXAMPLE 83

The procedure is as in Example 70, starting with 2-(2-pyridyl)-1,4-hydroxyquinoline (2.8 g), N,N-diethylcarbamoyl chloride (3.42 g), triethylamine (3.5 cc) and 4-dimethylaminopyridine (0.5 g) in anhydrous tetrahydrofuran (23 cc).

After chromatography of the residue on silica gel, using ethyl acetate as eluant, and crystallization in ethanol, 2-(2-pyridyl)-4-quinolyl diethylcarbamate (2.25 g), m.p. 100° C., is isolated.

2-(2-Pyridyl)-4-hydroxyquinoline can be prepared by the action of ethyl (pyridinecarbonyl)acetate (0.05 mole) on aniline (0.05 mole) at 160° C. in the presence of polyphosphoric acid (58 g). Its m.p. is 228° C.

EXAMPLE 84

The procedure is as in Example 52, starting with 2-phenyl-8-trifluoromethyl-4-quinolinol (6 g), N,N-diethyl-2-bromopropanamide (4.76 g) and potassium carbonate (6 g) in methyl ethyl ketone (400 cc).

After recrystallization of the residue in an ethyl acetate/isopropyl ether (1:4 by volume) mixture, N,N-diethyl-2-[(2-phenyl-8-trifluoromethyl-4-quinolyl)oxy]-propanamide (3 g), m.p. 146° C., is isolated.

2-Phenyl-8-trifluoromethyl-4-hydroxyquinoline can be prepared by the action of ethyl benzoylacetate (0.12 mole) on 2-trifluoromethylaniline (0.12 mole) at 140° C. in the presence of polyphosphoric acid (86 g). Its m.p. is 136° C.

EXAMPLE 85

Carbonyldiimidazole (1.65 g) is added to a stirred solution of dextrorotatory α-methyl-2-phenyl-4-quinazolinepropanoic acid (2 g) in tetrahydrofuran (20 cc). The mixture is stirred for about 20 minutes until the evolution of gas has ceased, and then for a further hour, and diethylamine (1.05 cc) is added. The mixture is stirred for 5 days at room temperature (approximately 20° C.) and then heated under reflux for two hours. The solvent is evaporated off under reduced pressure and the residue taken up with ethyl ether (100 cc). The organic phase is washed with water (2×10 cc), then with normal hydrochloric acid solution (2×5 cc), then with normal sodium hydroxide solution (2×5 cc) and finally with water (2×5 cc). It is then dried over magnesium sulphate and evaporated under reduced pressure. The residue is recrystallized twice in isopropyl ether. Laevorotatory N,N-diethyl-α-methyl-2phenyl-4-quinazolinepropanamide (1.1 g , m.p. 93.5° C., is thereby isolated; $\alpha_D$ at 0.5% in EtOH at 23° C.=−17.9°±2°.

Dextrorotatory α-methyl-2-phenyl-4-quinazolinepropanoic acid can be preoared by resolution of racemic α-methyl-2-pnenyl-4-quinatolinepropanoic acid by working in the following manner:

(1) Preparation of diastereoisomeric N-(1-phenyl-2-hydroxyethyl)-α-methyl -phenyl-4-quinazolinepropanamides.

2,2′-Dipyridyl disulphide (44.5 g) and (−)-α-phenylglycinol (28 g) are added under an atmosphere of nitrogen to a stirred solution of α-methyl-2-phenyl-4-quinazolinepropanoic acid (59.1 g) in methylene chloride (1800 cc). The mixture is cooled to about 0° C. and triphenylphosphine (53 g) is introduced in portions from a spatula in the course of 15 minutes. The mixture is stirred for 21 hours at room temperature (approximately 20° C.), the solvent removed under reduced pressure and the residue taken up with ethyl acetate (1800 cc). The organic phase is washed with normal sodium hydroxide solution (successively with 450 cc, then 200 cc and then 100 cc), and then with water (2×100 cc), and finally with 10% strength sodium dithionite solution (200 cc), water (100 cc) and saturated sodium chloride solution (100 cc). The organic phase is finally dried over magnesium sulphate and evaporated under reduced pressure. The residue is chromatographed under pressure on silica gel using a chloroform/toluene/diethylamine (50:44:6 by volume) mixture as eluant.

After recrystallization of the two diastereoisomeric amides in acetonitrile, there are obtained N-(1-phenyl-2-hydroxyethyl)-α-methyl-2-phenyl-4-quinazolinepropanamide, A form (18.1 g), m.p. 199° C., which is eluted first, and then N-(1-phenyl-2-hydroxyethyl)-α-methyl-2-phenyl-4-quinazolinepropanamide, B form (15.4 g), which is eluted subsequently and which has an m.p. of 204° C.

(2) Preparation of dextrorotatory α-methyl-2 -phenyl-4-quinazolinepropanoic acid:

N-(1-Phenyl-2-hydroxyethyl)-α-methyl-2-phenyl-4-quinazolinepropanamide, A form (19 g) in glacial acetic acid (90 cc) and concentrated hydrochloric acid solution (90 cc) are heated under reflux for one hour 30 minutes.

The acids are evaporated off under reduced pressure, and the residue is taken up with water (600 cc), alkalinised to pH 10 using concentrated ammonium hydroxide solution and washed with ethyl ether (100 cc). The aqueous phase is acidified to pH 5 with glacial acetic acid. The precipitate is filtered off, washed with water and dried. Dextrorotatory α-methyl-2-phenyl-4-quinazolinepropanoic acid (13.5 g), m.p. 179.1° C., is thereby obtained; $\alpha_D$ at 0.5% in glacial acetic acid=+4°±2° at 21° C.

EXAMPLE 86

The procedure is as in Example 85, starting with laevorotatory α-methyl-2-phenyl-4-quinazolinepropanoic acid (2 g) in tetrahydrofuran (20 cc), carbonyldiimidazole (1.65 g) and diethylamine (1.05 cc). After two recrystallizations in isopropyl ether, dextrorotatory N,N-diethyl-α-methyl-2-phenyl-4-quinazolinepropanamide (1.3 g), m.p. 93.8° C., is isolated.

$\alpha_D$ at 0.5% in EtOH at 23° C.=+17.8°±2°.

Laevorotatory α-methyl-2-phenyl-4-quinazolinepropanoic acid can be prepared like its dextrorotatory enantiomer described in Example 85, starting with N-(1-phenyl-2-hydroxyethyl)-α-methyl-2-phenyl-4-quinazolinepropanamide, B form (16.4 g), prepared according to Example 85, glacial acetic acid (80 cc) and concentrated hydrochloric acid solution (80 cc).

Laevorotatory α-methyl-2-phenyl-4-quinazolinepropanoic acid (11.4 g), m.p. 179.3° C., is obtained.

$\alpha_D$ at 0.5% in glacial acetic acid=−4°±2° at 21° C.

EXAMPLE 87

Carbonyldiimidazole (1.65 g) is added to a stirred solution of dextrorotatory α-methyl-2-phenyl-4-quinazolinepropanoic acid (2 g) in tetrahydrofuran (20 cc). The mixture is stirred for one hour at room temperature (until the evolution of gas has ceased) and N-methylisopropylamine (1.03 cc) is then added. The mixture is stirred for three days at room temperature (approximately 20° C.), then heated under reflux for 6 hours, N-methylisopropylamine (1.03 cc) is added and the mixture is heated under reflux for a further 12 hours. The treatment is then similar to that described in Example 85. After two recrystallizations in acetonitrile, laevorotatory N-isoprooyl-N-methyl-α-methyl-2-phenyl-4-quinazolinepropanamide (19 g), m.p. 171.2° C., is isolated; $\alpha_D$ at 0.5% in EtOH at 23° C.=−12.1°±2°.

EXAMPLE 88

The procedure is as in Example 87, starting with laevorotatory α-methyl-2-phenyl-4-quinazolinepropanoic acid (2 g) in tetrahydrofuran (20 cc), carbonyldiimidazole (1.65 g) and N-methylisopropylamine (1.03 cc).

After two recrystallizations in acetonitrile, dextrorotatory N-isopropyl-N-methyl-α-methyl-2-phenyl-4- quinazolinepropanamide (1.1 g), m.p. 171.0° C., is isolated.

$\alpha_D$ at 0.5% in EtOH at 23° C. = +16.3°±2°.

The drugs according to the invention consist of a compound of formula (I), a mixture of stereoisomeric compounds of formula (I) or, where it can exist, the salt of such a compound or mixture, in the pure state or in the form of a composition in which it is combined with any other pharmaceutically compatible product, which may be inert or physiologically active. These drugs according to the invention can be used orally, parenterally, rectally or topically.

As solid compositions for oral administration, tablets, pills, powders (gelatin capsules, wafer capsules) or granules can be used. In these compositions, the active principle according to the invention is mixed with one or more inert diluents such as starch, cellulose, sucrose, lactose or silica. These compositions can also contain substances other than diluents, e.g. one or more lubricants such as magnesium stearate or talc, a colouring, a coating (dragées) or a lacquer.

As liquid compositions for oral administration, it is possible to use solutions, suspensions, emulsions, syruos and elixirs which are pharmaceutically acceptable, containing inert diluents such as water, ethanol, glycerol, vegetable oils or liquid paraffin. These compositions can contain substances other than diluents, e.g. wetting agents, sweeteners, thickeners, flavourings or stabilizers.

The sterile compositions for parenteral administration can preferably be suspensions, emulsions or non-aqueous solutions. As a solvent or vehicle, it is possible to use water, propylene glycol, a polyethylene glycol, vegetable oils, especially olive oil, injectable organic esters, e.g. ethyl oleate, or other suitable organic solvents. These compositions can also contain adjuvants, especially wetting agents, tonicity regulators, emulsifiers, dispersants and stabilizers. The sterilization can be carried out in several ways, e.g. by aseptic filtration, by incorporating sterilizing agents in the composition, by irradiation or by heating. They can also be prepared in the form of sterile solid compositions which can be dissolved at the time of use in an injectable sterile medium.

The compositions for rectal administration are suppositories or rectal capsules which contain, in addition to the active product, excipients such as cocoa butter, semi-synthetic glycerides or polyethylene glycols.

The compositions for topical administration can be, e.g. creams, ointments, lotions, eyewashes, mouthwashes, nasal drops or aerosols.

In human therapy, the compounds according to the invention are especially useful as anxiolytics, anticonvulsants and antianginals, and for the treatment of immunodeficiency states.

The doses depend on the effects sought, the period of treatment and the administration route used; they are generally between 20 and 1000 mg per day orally for an adult, with unit doses ranging from 5 to 200 mg of active substance.

In general, the doctor will determine the appropriate dosage in terms of the age and weight and all the other factors specific to the subject to be treated.

The following examples illustrate compositions according to the invention:

EXAMPLE A

The customary technique is used to prepare gelatin capsules containing 50 mg doses of active product and having the following composition:

| | |
|---|---|
| N,N—Diethyl-2-[(2-phenyl-4-quinolyl)oxy]-propanamide | 50 mg |
| Cellulose | 18 mg |
| Lactose | 55 mg |
| Colloidal silica | 1 mg |
| Sodium carboxymethyl starch | 10 mg |
| Talc | 10 mg |
| Magnesium stearate | 1 mg |

EXAMPLE B

The customary technique is used to prepare tablets containing a 50 mg dose of active product and having the following composition:

| | |
|---|---|
| N,N—Diethyl-α-methyl-2-phenyl-4-quinazolinepropanamide | 50 mg |
| Lactose | 104 mg |
| Cellulose | 40 mg |
| Polyvidone | 10 mg |
| Sodium carboxymethyl starch | 22 mg |
| Talc | 10 mg |
| Magnesium stearate | 2 mg |
| Colloidal silica | 2 mg |
| Mixture of hydroxymethylcellulose, glycerin and titanium oxide (72:3.5:24.5) q.s. | 1 finished film-coated |
| | 245 mg tablet |

EXAMPLE C

An injectable solution is prepared containing 10 mg of active product and having the following composition:

| | |
|---|---|
| 3-Phenyl-1-isoquinolyl diethylcarbamate | 10 mg |
| Benzoic acid | 80 mg |
| Benzyl alcohol | 0.06 cc |
| Sodium benzoate | 80 mg |
| 95% strength ethanol | 0.4 cc |
| Sodium hydroxide | 24 mg |
| Propylene glycol | 1.6 cc |
| Water q.s. | 4 cc |

We claim:

1. A racemic or stereoisomeric compound of formula:

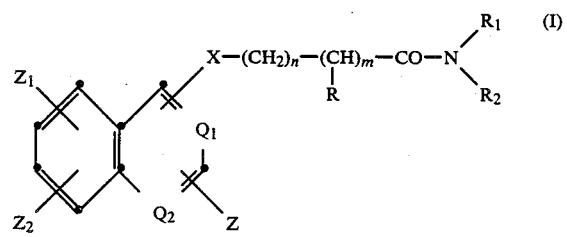

in which
Q₁ denotes a nitrogen atom,
Q₂ denotes a nitrgen atom,
Z₁ and Z₂, which may be identical or different, denote hydrogen, halogen, alkyl or alkoxy of 1 to 3 carbon atoms each, nitro, or trifluoromethyl,
Z is bound in the ortho or para position with respect to Q₂ and denotes phenyl, thienyl, pyridyl, or phenyl substituted by one or two substituents chosen from halogen, alkyl and alkoxy of 1 to 4 carbon atoms each, trifluoromethyl and nitro, the chain—X—(CH$_2$)$_n$—(CHR)$_m$—CONR$_1$R$_2$ is bound in the ortho or para position with respect to Q$_2$, R denotes hydrogen or alkyl of 1 to 3 carbon atoms, R$_1$ and R$_2$, which may be identical or different, denote a linear or branched alkyl of 1 to 6 carbon atoms each, cyloalkylalkyl of 3 to 6 carbon atom, phenyl, phenylakyl or cycloalkyl in each of which the alkyl contains 1 to 3 carbon atoms, and in which the cycloalkyl contains 3 to 6 carbon atoms, or alkenyl of 3 to 6 carbon atoms in which the double bond is not situated in the 1,2 position with respect to the nitrogen atom, R$_1$ and R$_2$ can also form, together with the nitrogen atom to which they are attached, a pyrrolidine, piperidine, morpholine or thiomorpholine ring, X denotes >CH—R$_3$, >N—R$_4$, >SO, >SO$_2$, oxygen, or sulphur, R$_3$ denotes hydrogen or alkyl of 1 to 3 carbon atoms, R$_4$ denotes alkyl of 1 to 3 carbon atoms, m is 0 or 1, and n is 0, 1 or 2, provided that, when X denotes >SO, >SO$_2$ or >N—R$_4$, the sum m+n is equal to at least 1, and, when Z is in the para position with respect to Q$_2$, X is not >CH—R$_3$, and also, where it can exist, a salt of such compound with an acid.

2. A racemic or stereoisomeric compound according to claim 1 in which Z$_1$ and Z$_2$, which may be identical or different, each denote hydrogen or alkyl of 1 to 3 carbon atoms, Z is bound in the ortho position with respect to Q$_2$ and denotes phenyl or phenyl substitued by alkyl or aloxy of 1 to 4 carbon atoms each, nitro, trifluoromethyl, or thienyl, the chain—X—(CH$_2$)$_n$—(CHR)$_m$—CO—NR$_1$R$_2$ is bound in the para position with respect to Q$_2$, R denotes hydrogen or alkyl of 1 to 3 carbon atoms, R$_1$ and R$_2$, which may be identical or different, each denote liner or branched alkyl of 1 to 6 carbon atoms each or phenyl, R$_1$ and R$_2$ can also form, together with the nitrogen atom to which they are attached, a piperidine or morpholine ring, X deontes CH—R$_3$, oxygen or sulphur, R$_3$ denotes hydrogen, m equals 0 or 1, n equals 0, 1 or 2, and also, where it can exist, a salt of such a compound with an acid.

3. A compound according to claim 1 which is N,N-diethyl-α-methyl-2-phenyl-4-quinazolinepropanamide.

4. A compound according to claim 1 which is N-methyl-N-phenyl-2-phenyl-4-quinoazolinepropanamide.

5. A compound according to claim 1 which is N,N-diethyl-8-methyl-2-phenyl-4-quinazoliniepropanamide.

6. A compound according to claim 1 which is N,N-diethyl-(2-phenyl-4-quinazolinyl)oxyacetamide.

7. A compound according to claim 1 which is N,N-diethyl-2-[(2-phenyl-4-quinazolinyl)oxy]propanamide.

8. A compound according to claim 1, which is dextrorotatory N,N-diethyl-2-[(2-phenyl-4-quinazolinyl)oxy]-propanamide.

9. A compound according to claim 1 which is N,N-diethyl-2-phenyl-4-quinazolinepropanamide.

10. A pharmaceutical composition containing in association with one or more diluents or adjuvants which are compatible and pharmaceutically acceptable, at least one active ingredient of formula:

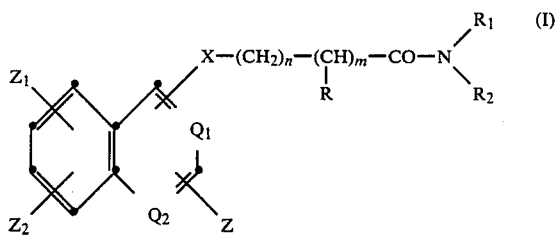

in which

Q$_1$ denotes nitrogen,

Q$_2$ denotes nitrogen,

Z$_1$ and Z$_2$, which may be identical or different, denote hydrogen, halogen, alkyl or alkoxy of 1 to 3 carbon atoms each, nitro, or trifluoromethyl, Z is bound in the ortho or para position with respect to Q$_2$ and deontes phenyl, thienyl, pyridyl or phenyl substituted by one or two substituents chosen from halogen, alkyl and alkoxy of 1 to 4 carbon atoms each, trifluoromethyl and nitro, the chain—X—(CH$_2$)$_n$—(CHR)$_m$—CO—NR$_1$R$_2$ is bound in the ortho position or para position with respect to Q$_2$, R denotes hydrogen or alkyl of 1 to 3 carbon atoms, R$_1$ and R$_2$, which may be identical or different, denote a linear or branched alkyl of 1 to 6 carbons atoms each, cycloalkyl of 3 to 6 carbon atoms, phenyl, phenylalkyl or cycloalkylalkyl in each of which the alkyl contains 1 to 3 carbon atoms and in which the cycloalkyl contains 3 to 6 carbon atoms or an alkenyl of 3 to 6 carbon atoms in which the double bond is not situated in the 1,2 position with respect to the nitrogen atom, R$_1$ and R$_2$ can also form, together with the nitrogen atom to which they are attached, a pyrrolidien, piperidine, morpholine or thiomorpholine ring, X denotes >CH—R$_3$, >N—R$_4$, >SO or >SO$_2$, oxygen, or sulphur, R$_3$ denotes hydrogen or alkyl of 1 to 3 carbon atoms, R$_4$ denotes alkyl of 1 to 3 carbon atoms, m is 0 or 1, and n is 0, 1 or 2, provided that, when X denotes >SO, >SO$_2$ or >N—R$_4$, the sum m+n is equal to at least 1, and, when Z is in the para position with respect to Q$_2$, X cannot denote >CH—R$_3$, or a mixture of stereoisomeric compounds of formula (I), or, where it can exist, a salt of such a compond or of a mixture of stereoisomeric compounds with a pharmaceutically acceptable acid.

11. A pharmaceutical composition according to claim 10 containing a compound of the formula (I) in which Z$_1$ and Z$_2$, which may be identical or different, each denote hydrogen or alkyl of 1 to 3 carbon atoms, Z is bound in the ortho position with respect to Q$_2$ and denotes phenyl or phenyl substituted by alkyl or alkoxy of 1 to 4 carbon atoms each, nitro, trifluoromethyl, or thienyl, the chain —X—(CH$_2$)$_n$—(CHR)$_m$—CO—NR$_1$R$_2$ is bound in the para position with respect ot Q$_2$, R denotes hydrogen or alkyl of 1 to 3 carbon atoms, R$_1$ and R$_2$, which may be identical or different, each denote linear or branched alkyl of 1 to 6 carbon atoms each or phenyl, $R_1$ and $R_2$ can also form, together with the nitrogen atom to which they are attached, a piperiidne or morpholine ring, X denotes CH—$R_3$, oxygen or sulphur $R_3$ deontes hydrogen, m equals 0 or 1, n equals 0, 1 or 2, and also, where it can exist, a salt of such a compound or of a mixture of setereoisomeric compounds with a pharmaceutically acceptable acid.

12. Method of treating a subject in need of anxiolytic, therapy which comprises amdinistering to such subject an effective amount of a compound as claimed in claim 1.